United States Patent
Edelman et al.

(10) Patent No.: US 7,694,693 B1
(45) Date of Patent: Apr. 13, 2010

(54) MIXING VALVE FOR A CONTRAST THERAPY SYSTEM

(75) Inventors: Howard Edelman, San Francisco, CA (US); Daqing Liu, Foster City, CA (US)

(73) Assignee: VitalWear, Inc., South San Francisco, CA (US)

( * ) Notice: Subject to any disclaimer, the term of this patent is extended or adjusted under 35 U.S.C. 154(b) by 1169 days.

(21) Appl. No.: 11/291,517

(22) Filed: Nov. 30, 2005

Related U.S. Application Data

(63) Continuation-in-part of application No. 10/267,247, filed on Oct. 8, 2002, now Pat. No. 7,211,104.

(51) Int. Cl.
    *F16K 11/087* (2006.01)
(52) U.S. Cl. .................. 137/625.41; 137/625.3
(58) Field of Classification Search ............ 137/625.16, 137/625.3, 625.41, 625.42, 625.47
    See application file for complete search history.

(56) References Cited

U.S. PATENT DOCUMENTS

| | | | |
|---|---|---|---|
| 26,663 A | 1/1860 | French | |
| 128,220 A | 6/1872 | Gardner et al. | |
| 267,435 A | 11/1882 | Leiter | |
| 301,931 A | 7/1884 | Smith et al. | |
| 430,721 A | 6/1890 | Winkler | |
| 691,270 A | 1/1902 | Jones | |
| 787,920 A | 4/1905 | Hofmann | |
| 889,964 A | 6/1908 | Powell | |
| 1,313,105 A * | 8/1919 | Moran | 137/625.41 |
| 1,817,277 A | 8/1931 | Uhlig | |
| 2,322,449 A | 6/1943 | Johnson et al. | |
| 2,451,218 A | 10/1948 | Hengst | |
| 2,504,569 A | 4/1950 | Murphy et al. | |
| 2,518,299 A | 8/1950 | Fernandez | |
| 2,666,656 A | 1/1954 | Bruning | |
| 2,726,658 A | 12/1955 | Chessey | |
| 2,773,531 A | 12/1956 | La Verne Johnson | |
| 2,854,027 A * | 9/1958 | Kaiser et al. | 137/625.41 |
| 2,896,977 A | 7/1959 | Hansen | |
| 2,911,974 A | 11/1959 | Spence | |
| 3,132,688 A | 5/1964 | Nowak | |
| 3,140,365 A | 7/1964 | Voland | |
| 3,191,972 A | 6/1965 | Collar | |
| 3,283,780 A | 11/1966 | Sutton | |
| 3,284,842 A | 11/1966 | Jennings, Jr. | |
| 3,410,487 A * | 11/1968 | Hyde | 239/26 |
| 3,460,801 A | 8/1969 | Norton | |
| 3,469,595 A * | 9/1969 | Petursson | 137/100 |
| 3,548,819 A | 12/1970 | Davis et al. | |

(Continued)

FOREIGN PATENT DOCUMENTS

DE    3343664    3/1985

(Continued)

*Primary Examiner*—John Fox
(74) *Attorney, Agent, or Firm*—Kang S. Lim

(57) ABSTRACT

The present invention relates to fluid mixing valves, and more particularly, to mixing valve assemblies which incorporate a ball element and which are adapted for use in a thermal or contrast therapy system, or medical thermal therapy system. The ball element of the present invention is characterized by continuously varying restrictive inlets which enable the user to obtain a substantially linear therapy temperature profile while maintaining substantially constant outlet pressure and flow rates.

15 Claims, 13 Drawing Sheets

U.S. PATENT DOCUMENTS

| | | | |
|---|---|---|---|
| 3,556,470 A | 1/1971 | Ehrens | |
| 3,586,048 A | 6/1971 | Arnold | |
| 3,612,059 A | 10/1971 | Ersek | |
| 3,648,765 A | 3/1972 | Starr | |
| 3,683,902 A | 8/1972 | Artemenko et al. | |
| 3,744,555 A | 7/1973 | Fletcher et al. | |
| 3,788,348 A | 1/1974 | Johnson | |
| 3,869,871 A | 3/1975 | Rybalko et al. | |
| 3,871,381 A | 3/1975 | Roslonski | |
| 3,886,936 A | 6/1975 | Wehrenberg | |
| 3,901,225 A | 8/1975 | Sconce | |
| 3,916,929 A | 11/1975 | Brown | |
| 3,987,819 A * | 10/1976 | Scheuermann | 137/637.3 |
| 3,993,053 A | 11/1976 | Grossan | |
| 3,995,621 A | 12/1976 | Fletcher et al. | |
| 4,099,522 A | 7/1978 | Alenares | |
| 4,149,529 A | 4/1979 | Copeland et al. | |
| 4,149,541 A | 4/1979 | Gammons et al. | |
| 4,184,537 A | 1/1980 | Sauder | |
| 4,196,772 A | 4/1980 | Adamski et al. | |
| 4,273,290 A | 6/1981 | Quinn | |
| 4,338,944 A | 7/1982 | Arkans | |
| 4,459,468 A | 7/1984 | Bailey | |
| 4,475,573 A * | 10/1984 | Hindman | 137/625.41 |
| 4,552,132 A | 11/1985 | Ruscigno | |
| 4,587,959 A | 5/1986 | Ruderian | |
| 4,669,476 A | 6/1987 | Gordon et al. | |
| 4,691,762 A | 9/1987 | Elkins et al. | |
| 4,703,957 A | 11/1987 | Blenkush | |
| 4,733,692 A | 3/1988 | Kotake et al. | |
| 4,823,651 A | 4/1989 | England | |
| 4,844,072 A | 7/1989 | French et al. | |
| 4,846,176 A | 7/1989 | Golden | |
| 4,877,181 A | 10/1989 | Stewart | |
| 4,910,978 A | 3/1990 | Gordon et al. | |
| 4,913,316 A | 4/1990 | Richter | |
| 4,962,761 A | 10/1990 | Golden | |
| 4,989,790 A | 2/1991 | Martin et al. | |
| 5,005,604 A * | 4/1991 | Aslanian | 137/556 |
| 5,013,013 A | 5/1991 | Spedding | |
| 5,038,852 A | 8/1991 | Johnson et al. | |
| 5,051,562 A | 9/1991 | Bailey et al. | |
| 5,072,875 A | 12/1991 | Zacoi | |
| 5,077,980 A | 1/1992 | Weber | |
| 5,080,089 A | 1/1992 | Mason et al. | |
| 5,086,771 A | 2/1992 | Molloy | |
| 5,143,064 A | 9/1992 | Cochran | |
| D331,115 S | 11/1992 | Stout | |
| D333,350 S | 2/1993 | Redira, Jr. | |
| 5,183,039 A | 2/1993 | Sarian et al. | |
| 5,230,335 A | 7/1993 | Johnson, Jr. et al. | |
| 5,232,020 A | 8/1993 | Mason et al. | |
| 5,234,166 A | 8/1993 | Foster et al. | |
| D344,343 S | 2/1994 | McNew | |
| 5,314,455 A | 5/1994 | Johnson, Jr. et al. | |
| 5,316,041 A | 5/1994 | Ramacier, Jr. et al. | |
| 5,324,318 A | 6/1994 | Smith | |
| 5,324,319 A | 6/1994 | Mason et al. | |
| 5,330,519 A | 7/1994 | Mason et al. | |
| 5,344,436 A | 9/1994 | Fontenot et al. | |
| 5,368,234 A | 11/1994 | Foster et al. | |
| 5,372,608 A | 12/1994 | Johnson | |
| 5,383,919 A | 1/1995 | Kelly et al. | |
| 5,386,823 A | 2/1995 | Chen | |
| D358,216 S | 5/1995 | Dye | |
| 5,411,541 A | 5/1995 | Bell et al. | |
| 5,417,720 A | 5/1995 | Mason | |
| 5,433,083 A | 7/1995 | Kuramarohit | |
| 5,439,473 A | 8/1995 | Jorgensen | |
| 5,441,533 A | 8/1995 | Johnson et al. | |
| 5,449,379 A | 9/1995 | Hadtke | |
| 5,456,701 A | 10/1995 | Stout | |
| 5,466,250 A | 11/1995 | Johnson, Jr. et al. | |
| 5,466,251 A | 11/1995 | Brunson et al. | |
| 5,476,489 A | 12/1995 | Koewler | |
| 5,486,207 A | 1/1996 | Mahawili | |
| 5,499,766 A | 3/1996 | Foster et al. | |
| 5,507,792 A | 4/1996 | Mason et al. | |
| D369,866 S | 5/1996 | Baughn | |
| 5,555,579 A | 9/1996 | Wu | |
| 5,562,604 A | 10/1996 | Yablon et al. | |
| 5,601,651 A * | 2/1997 | Watabe | 118/715 |
| 5,603,728 A | 2/1997 | Pachys | |
| 5,617,811 A | 4/1997 | Johnson | |
| 5,647,051 A | 7/1997 | Neer | |
| 5,662,695 A | 9/1997 | Mason et al. | |
| 5,668,565 A | 9/1997 | Robinson | |
| 5,711,155 A | 1/1998 | DeVilbiss et al. | |
| RE35,744 E | 3/1998 | Foster et al. | |
| D393,719 S | 4/1998 | Nichols | |
| 5,741,220 A | 4/1998 | Brink | |
| 5,755,275 A | 5/1998 | Rose et al. | |
| 5,755,733 A | 5/1998 | Morita | |
| 5,755,755 A | 5/1998 | Panyard | |
| 5,865,841 A | 2/1999 | Kolen et al. | |
| 5,891,188 A | 4/1999 | Maytal | |
| 5,894,615 A | 4/1999 | Alexander | |
| 5,904,291 A | 5/1999 | Knapp | |
| 5,968,072 A | 10/1999 | Hite et al. | |
| 6,050,297 A | 4/2000 | Ostrowski et al. | |
| 6,117,164 A | 9/2000 | Gildersleeve et al. | |
| 6,149,617 A | 11/2000 | McNally et al. | |
| 6,270,055 B1 | 8/2001 | Szeteli et al. | |
| 6,295,819 B1 | 10/2001 | Mathiprakasam et al. | |
| 6,299,626 B1 | 10/2001 | Viranyi | |
| 6,352,550 B1 | 3/2002 | Gildersleeve et al. | |
| 6,440,159 B1 | 8/2002 | Edwards et al. | |
| 6,551,347 B1 | 4/2003 | Elkins | |
| 6,699,267 B2 | 3/2004 | Voorhees et al. | |
| 6,827,728 B2 | 12/2004 | Ellingboe et al. | |
| 6,880,575 B2 * | 4/2005 | Mountford et al. | 137/625.41 |
| 6,957,697 B2 | 10/2005 | Chambers | |
| 7,000,682 B2 | 2/2006 | Chambers | |
| 7,191,798 B2 | 3/2007 | Edelman et al. | |
| 7,211,104 B2 | 5/2007 | Edelman | |
| 2001/0018604 A1 | 8/2001 | Elkins | |
| 2001/0039439 A1 | 11/2001 | Elkins et al. | |
| 2002/0019657 A1 | 2/2002 | Elkins | |
| 2002/0026226 A1 | 2/2002 | Ein | |
| 2002/0032473 A1 | 3/2002 | Kushnir et al. | |
| 2004/0068310 A1 | 4/2004 | Edelman | |

FOREIGN PATENT DOCUMENTS

| | | |
|---|---|---|
| DE | 3410413 | 10/1985 |
| GB | 2 175 496 A | 12/1986 |
| IT | 246899 | 3/1926 |
| SU | 577-350 | 10/1997 |

\* cited by examiner

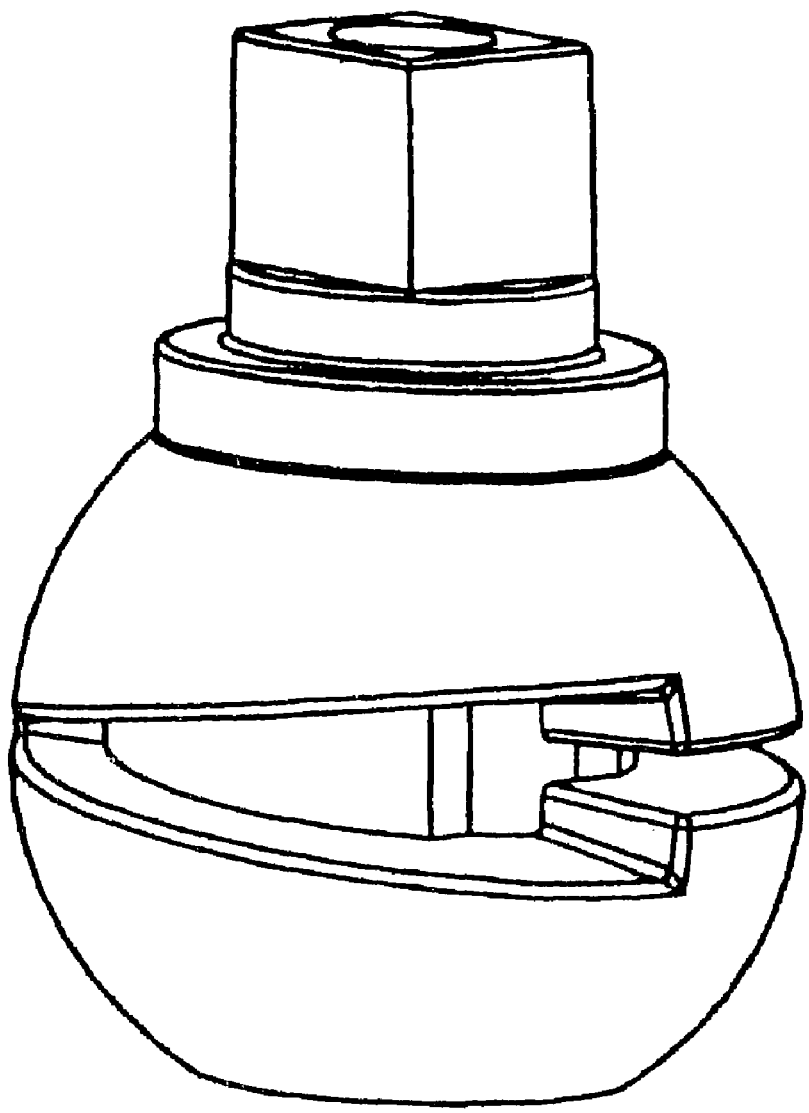
FIG. 10

MIXING VALVE FOR A CONTRAST THERAPY SYSTEM

CROSS REFERENCE TO RELATED APPLICATIONS

This is a continuation-in-part of U.S. application Ser. No. 10/267,247 filed on Oct. 8, 2002 now U.S. Pat. No. 7,211,104, entitled "Contrast Therapy System and Method", which is hereby fully incorporated by reference.

TECHNICAL FIELD

The present invention relates to fluid mixing valves, and more particularly, to mixing valve assemblies which incorporate a ball element and which are adapted for use in a thermal or contrast therapy system, or medical thermal therapy system. The ball element of the present invention is characterized by continuously varying restrictive inlets which enable the user to obtain a substantially linear therapy temperature profile while maintaining substantially constant outlet pressure and flow rates.

BACKGROUND OF THE INVENTION

Numerous thermal therapy devices that apply external treatments to the body are known in the art. Thermal or contrast therapy devices deliver or remove heat to a given therapy area for an effective amount of time in order to achieve a desired therapeutic result. Contrast therapy devices are used to reduce swelling or to encourage healing after swelling has receded. They are also used to soothe muscle and joint pain through the application of heat and compression therapy. Application of heat or cold may be used to heal and rehabilitate injuries to bone, muscle, ligaments, tendons and skin. Cold therapy may be used to reduce swelling, decrease pain, and promote healing of injured tissue. Heat therapy can be used to relax joint tissue, such as ligaments and tendons, to increase range of motion. Thermal therapy can also be used after surgery to reduce pain and swelling and promote healing.

While applying hot and/or cold to sore body parts as therapeutic treatment is well known, the ability to effectively control the therapy temperature of the particular treatment has been problematic. The potential effectiveness of a hot or cold treatment increases as the level of control for the treatment increases. In particular, the effectiveness depends on the ability to control the temperature. If cold treatments are too cold, they may cause skin and tissue damage. Similarly, if hot treatments are too hot, they may burn or otherwise damage the recipient. Therefore, systems for precisely controlling the temperature of a therapy are desirable.

Prior art devices have been developed to deliver hot or cold fluids for therapeutic purposes. For example, U.S. Pat. No. 6,551,347 discloses a heat exchange splint and control unit with a single fluid reservoir and a mixing valve that receives a single input fluid and selectively diverts a first portion of the input fluid to a heat exchanger, while a second portion is diverted past the heat exchanger. The fluid portions recombine at a Y junction, and the temperature of the combined fluid is determined by the relative amount of fluid diverted to the heat exchanger compared to the amount of fluid bypassing the heat exchanger and flowing straight to the Y junction. The temperature of the combined fluid may be set as low as the heat exchanger permits and may achieve a maximum temperature equal to the ambient temperature of the surrounding environment.

Prior art devices have also been developed to alternately deliver hot and cold fluids for therapeutic purposes. For example, U.S. Pat. No. 6,295,819 discloses a thermoelectric heat pump fluid circuit with a single fluid reservoir and a valve that may be selectively toggled between two positions for delivering either a hot or cold fluid. The position of the valve determines which of two fluid temperatures are output by controlling the direction of fluid flow around a heat pump. When the valve is switched, the temperature of fluid in the system gradually shifts form one of two possible therapy temperatures to the other.

The prior art devices do not provide a means for incrementally controlling the output temperature of the therapy fluid supplied to a compressive heat therapy device. Furthermore, there remains a need for a thermal therapy system which includes a means for achieving linear control of the output temperature of a therapy fluid. Previous efforts to provide thermal therapy have included U.S. Pat. No. 2,531,074 which provides a therapy pad wherein heated or cooled water is alternately injected. U.S. Pat. No. 4,149,529 also teaches delivering hot or cold fluid to a compressive therapy device. U.S. Pat. No. 4,756,299 provides a heating pad with various sized holes on its opposite sides. The two sides offer the therapy recipient two different temperatures at which to uses the product.

Systems that can achieve a desired set temperature and do so rapidly, can further increase the benefit of the applied therapy. This is because such systems can be used to avoid the onset of reflex vasodilatation while still giving the analgesic benefits of vasoconstriction. Cold therapy temperatures as high as 40-50 degrees Fahrenheit may induce vasodilatation as the body attempts to warm the effected area. This is know as the 'hunting effect.' In order to avoid the hunting effect, but still gain the analgesic benefits of vasoconstriction, a carefully selected cold therapy temperature must be achieved. Generally, a cold therapy temperature of about 55 degrees Fahrenheit will give the benefits of vasoconstriction while avoiding the hunting effect, however, this temperature can vary according to each individual's physiology.

While the above described therapy pads provide for thermal therapy, they are not effective at providing a convenient mixing valve means for controlling the temperature of the delivered therapy fluid. Previous efforts do not provide for linear control of therapy fluid temperature over the range of achievable temperatures. Known thermal therapy mixing valves are only effective at controlling therapy fluid temperatures at the high and low temperature extremes. There remains a need for a thermal therapy system with a mixing valve assembly capable of providing incremental control of therapy fluid temperature changes giving a linear temperature profile over the full range of therapy temperatures.

SUMMARY OF THE INVENTION

To achieve the foregoing and in accordance with the present invention, thermal therapy system mixing valve assemblies and methods for providing a temperature regulated fluid are provided. Such systems are useful for providing effective thermal therapy through precise temperature control of therapy fluid.

According to one aspect of the present invention, a thermal or contrast therapy system includes a hot reservoir for holding a relatively hot fluid and a cold reservoir for holding a relatively cold fluid. The system also includes a mixing valve for receiving a selected ratio of the hot and cold fluids from the hot and cold reservoirs. The mixing valve is operable to deliver a therapy fluid with a therapy temperature determined by the selected ratio. The system also includes a therapy pad for receiving the therapy fluid form the mixing valve and returning the therapy fluid to at least one of the hot reservoir and the cold reservoir.

In one embodiment, the system includes a mixing valve assembly operable to deliver a therapy fluid with a therapy temperature determined by a selected ratio of relatively high temperature and relatively low temperature fluids. The assembly includes an incrementally positionable ball vale element having an adjustable rotational position in the assembly. The ball has a first inlet and a second inlet for high and low temperature fluids, respectively. The ball also has a mixing chamber in fluid communication with both inlets, and an outlet in fluid communication with the mixing chamber. In this embodiment, the selected ratio of high and low temperature fluids is determined by the rotational position of the ball.

In another embodiment, the selected ratio and, by extension, therapy fluid temperature (hereinafter "therapy temperature") is incrementally controlled by adjusting the rotational position of the ball. In this embodiment, the incremental rotation of the ball produces a substantially liner change in therapy temperature over time.

In yet another embodiment of the instant invention, the first and second inlets are substantially wedge shaped. The inlets are characterized by a wide forward edge and a narrow rear apex. Preferably, the second inlet is larger than the first inlet. More preferably, the second inlet is substantially larger than the first inlet.

In another aspect of the present invention, the ball element is further characterized by spaced apart interior restrictor walls defining distal inlet chambers and an interior mixing chamber. The restrictor walls act to channel the high and low temperature fluids from the inlet chambers to the mixing chamber. The restrictor wall defining the low temperature fluid inlet chamber extends further around the interior of the mixing valve than the wall defining the high temperature fluid inlet chamber.

In a preferred embodiment, the wide forward edge of the first wedge shaped inlet forms a 5° opening at the surface of the mixing ball, while the wide forward edge of the second wedge shaped inlet forms a 15° opening. In this embodiment, both wedged inlets extend 140° around the surface of the ball.

The present invention also provides a method for supplying a temperature-regulated fluid to a therapy recipient. The method includes providing a volume of fluid at a relatively high temperature, providing a fluid at a relatively low temperature, and providing a fluid pathway for each fluid. The fluid pathway passes through a mixing valve assembly including an incrementally positionable ball element. The method includes incrementally adjusting the rotational position of the ball to give linear control of the therapy temperature over a given temperature range. Preferably, the temperature range extends from the temperature of the low temperature fluid to the temperature of the high temperature fluid.

Note that the various features of the present invention described above can be practiced alone or in combination. These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which:

FIG. 10 is an isometric view of a ball element in accordance with an embodiment of the present invention.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

Figure 7:
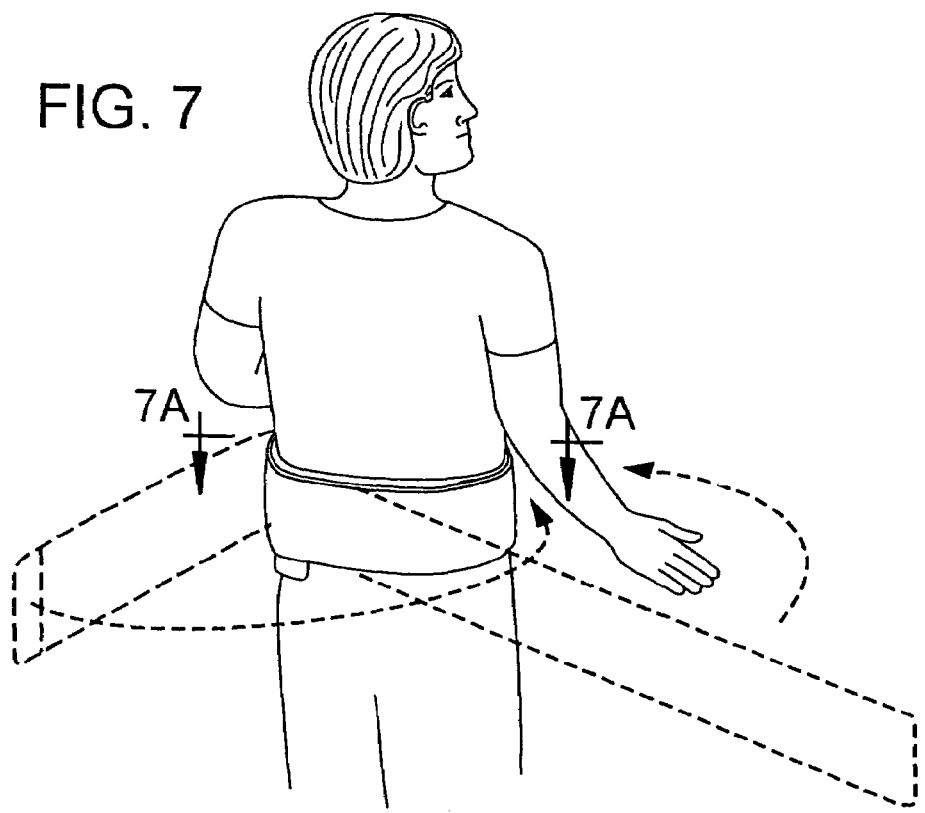
FIG. 7 is an isometric view of a therapy pad wrapped around a therapy recipient.
Figure 8:
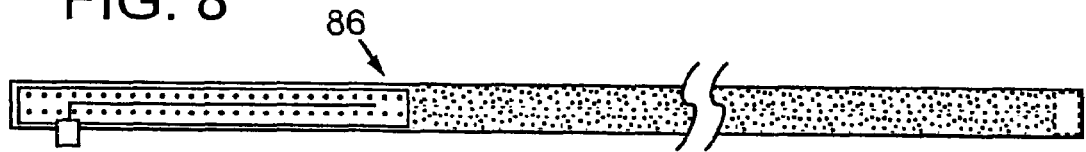
FIG. 8 is a plan view of a contrast therapy pad in accordance with an embodiment of the present invention.
Figure 9:
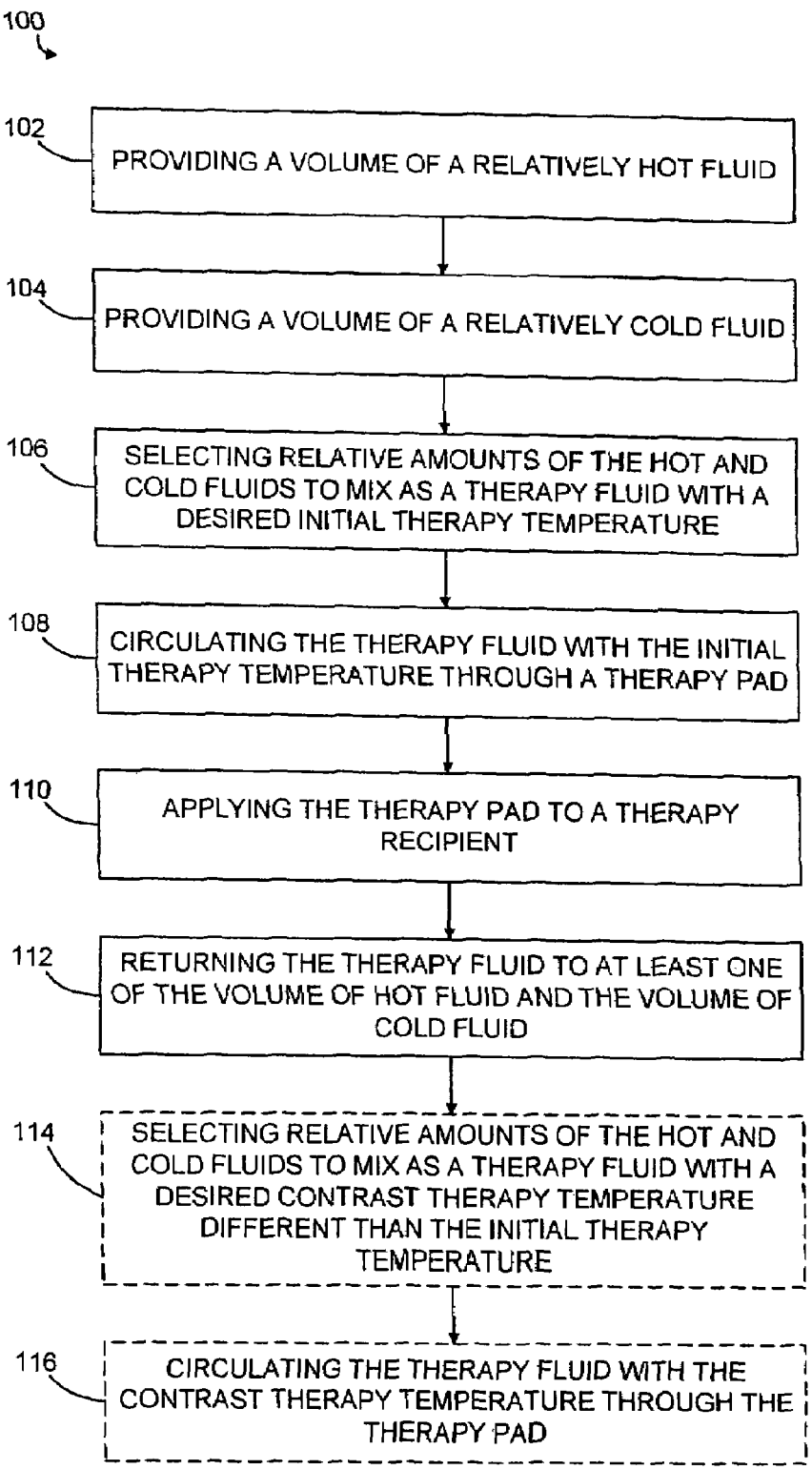
FIG. 9 is an illustration of a method for administering contrast therapy to a therapy recipient in accordance with an embodiment of the present invention.
Figure 14:
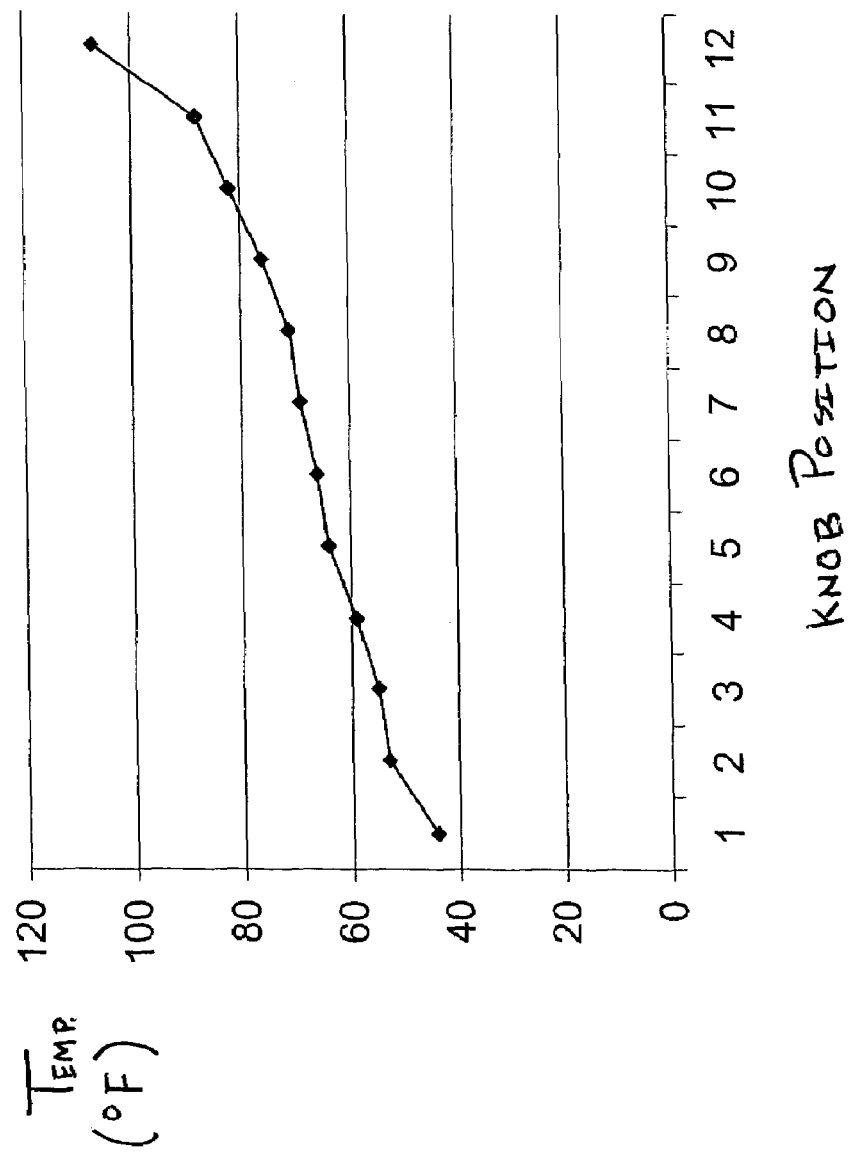
FIG. 14 is a graph illustrating the change in temperature over time of a therapy fluid exiting a mixing valve assembly element.
Figure 15:
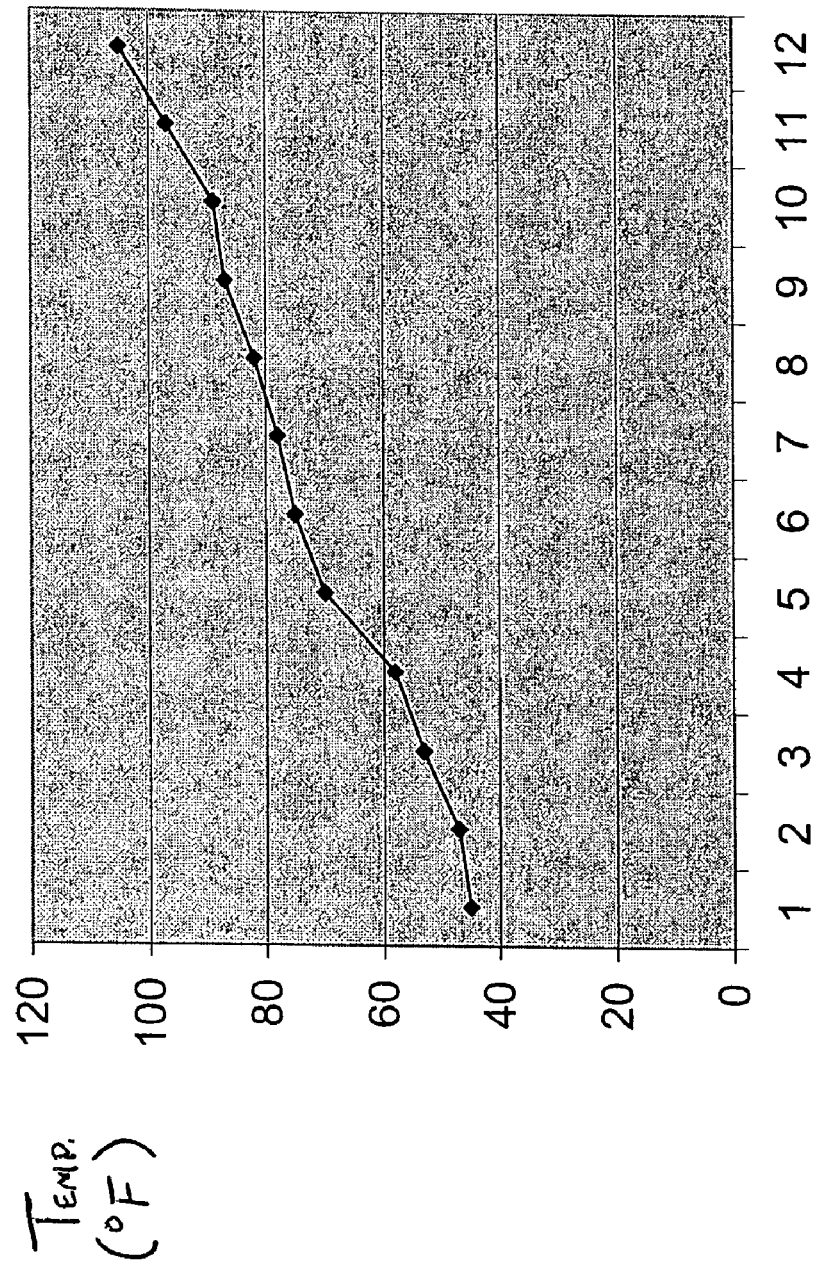
FIG. 15 is a graph illustrating the change in temperature over time of a therapy fluid exiting a mixing valve assembly element in accordance with an embodiment of the present invention.

To facilitate discussion, FIGS. 1 through 8 show various views of the present contrast therapy system. FIG. 9 provides an illustration of a method for providing contrast therapy to a therapy recipient. FIGS. 10 through 14B provide various views of the present mixing valve assembly and the present ball element. FIGS. 15 through 17 show graphs illustrating the change in temperature over time of a therapy fluid exiting a mixing valve assembly element in accordance with various embodiments of the present invention.

The present invention relates to a contrast therapy system and a method of providing contrast therapy. An embodiment of the present invention is shown generally at 10 in FIG. 1. Although useful for applying any combination of heat, cold, and compression, to a recipient for virtually any reason, the contrast therapy system described below demonstrates particular utility for treating sore, strained, arthritic, injured, heavily exercised, and/or otherwise taxed body parts. The contrast therapy system is described below in the context of providing "therapy" to a recipient, however, it should be understood that the contrast therapy system is equally well suited for providing any combination of heat, cold, and compression for what may be considered non-therapeutic purposes.

As described herein, the contrast therapy system is capable of imparting a desired therapy temperature to a therapy pad 22, which may be applied to a therapy recipient. The system is capable of shifting the therapy temperature between hot and cold temperatures very quickly, which has proven to be beneficial. The precise temperature may be set at any temperature between controlled maximum and minimum temperatures. The system is also capable of applying compressive force to a therapy recipient, thus increasing the effectiveness of treatments. Furthermore, the contrast therapy system may be designed as a relatively small portable unit, as shown at 30 of FIG. 1, which is both easy and inexpensive to operate.

Fluid Circuit

Figure 2:
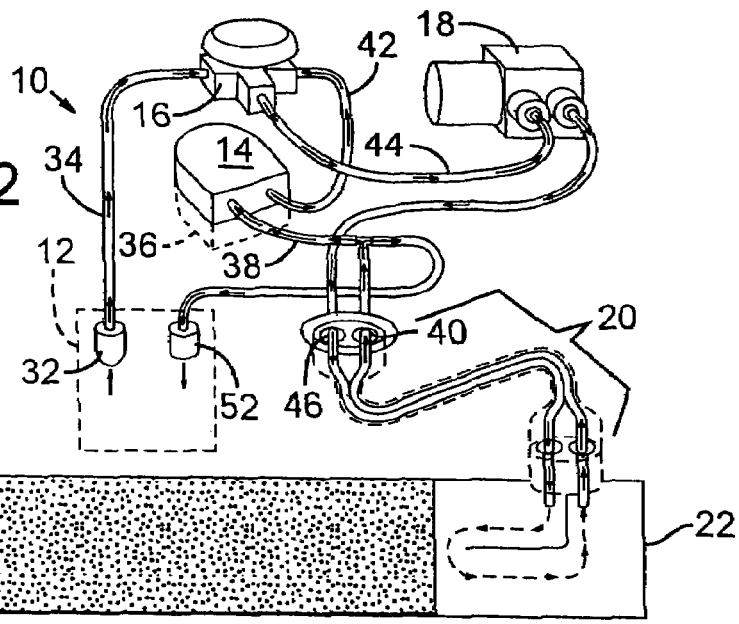
FIG. 2 is a schematic view of a fluid circuit for administering contrast therapy in accordance with an embodiment of the present invention.
Figure 3:
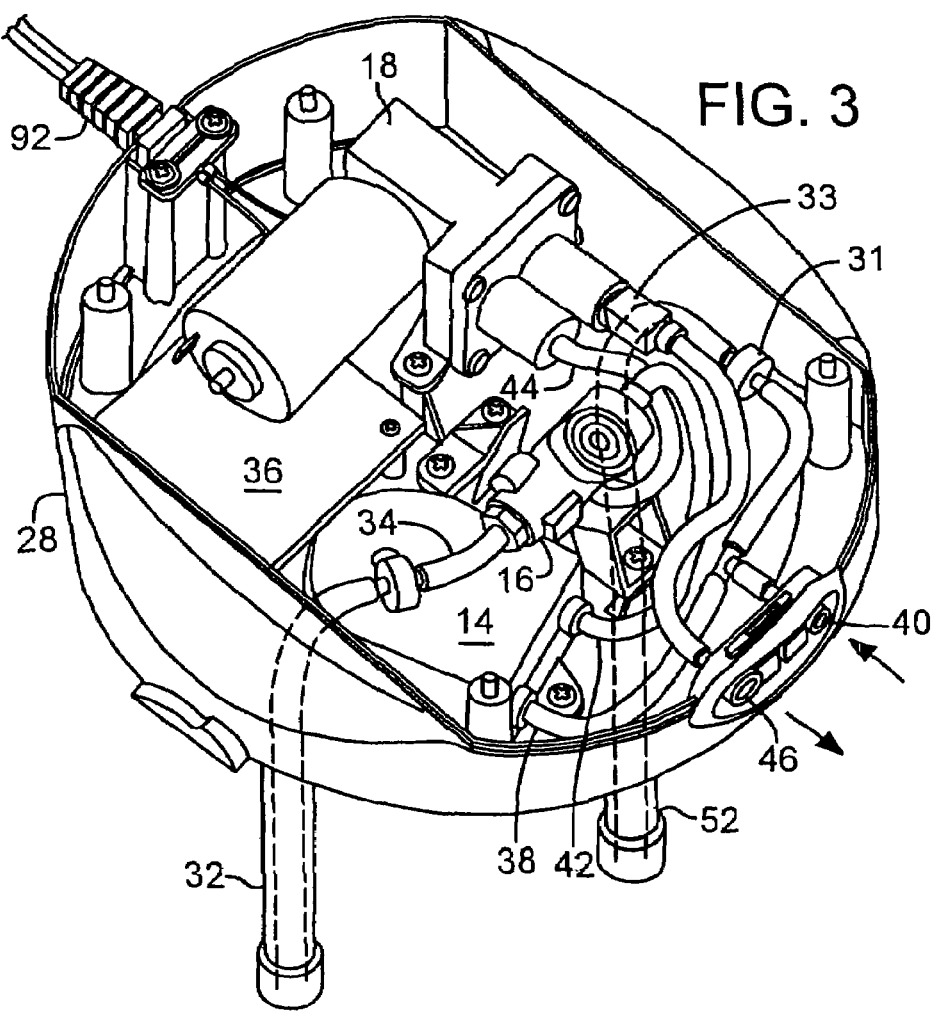
FIG. 3 is an isometric view of the fluid circuit of FIG. 2 housed within the lid portion of the contrast therapy system of FIG. 1.

FIG. 2 schematically shows a fluid circuit of a contrast therapy system 10, and FIG. 3 shows such a circuit housed by a lid 28 of a portable control unit 30. As illustrated in FIGS. 2 and 3, contrast therapy system 10 includes a cold reservoir 12, hot reservoir 14, mixing valve 16, pump 18, fluidic coupling assembly 20, and therapy pad 22. As described in detail below, the contrast therapy system is designed to control the temperature of a therapy fluid that circulates through therapy pad 22. Mixing valve 16 selectively combines fluid received from the cold and hot reservoirs and passes the combined fluid to the therapy pad as a therapy fluid. The mixing valve may control the temperature of the therapy fluid, changing between hot and cold temperatures in a short period of time.

Figure 1:
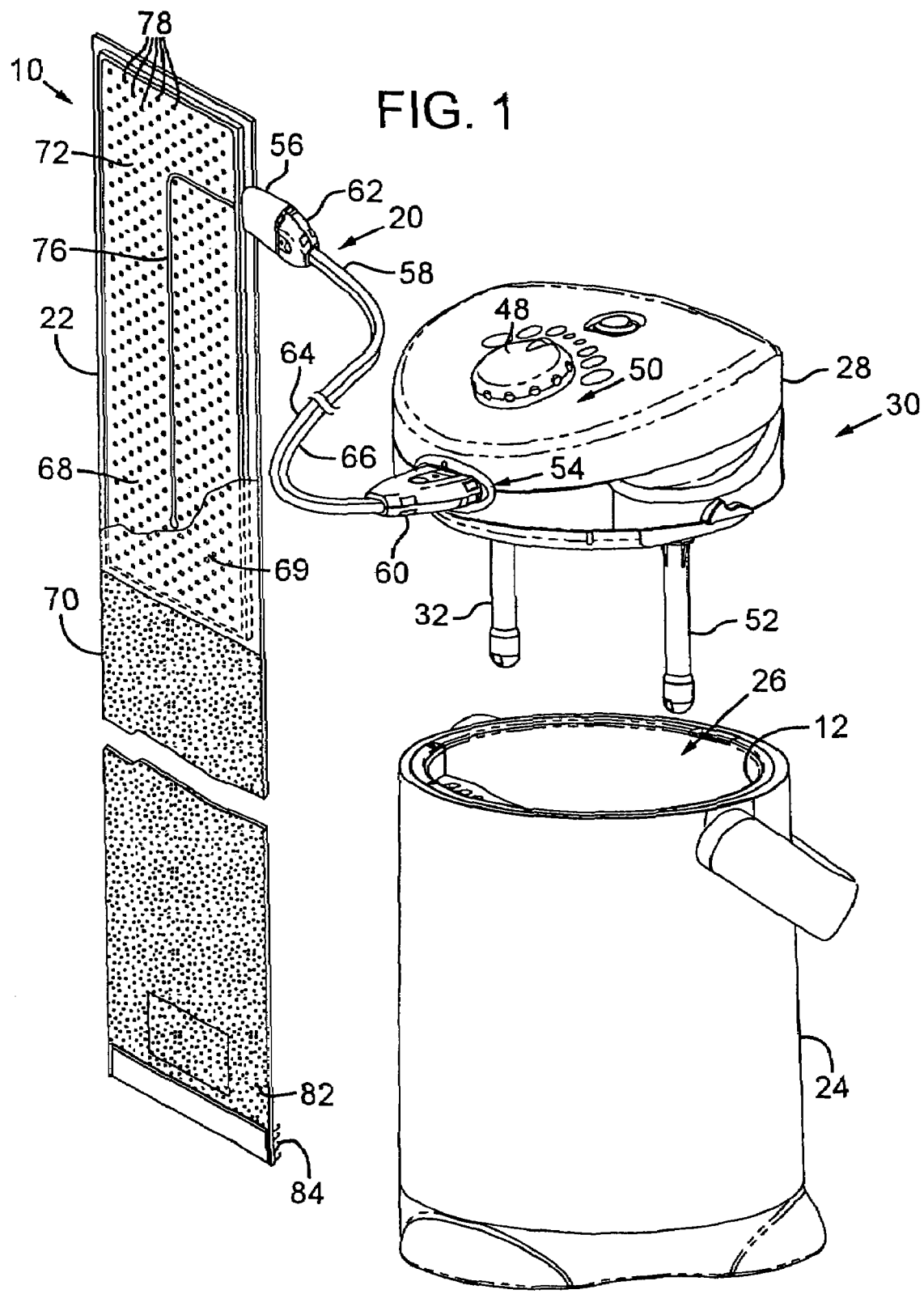
FIG. 1 is an isometric view of one embodiment of the contrast therapy system in accordance with the present invention.

Cold reservoir 12 is designed to hold a relatively cold fluid, which may be passed to a mixing valve and eventually to a therapy pad. As shown in FIG. 1, cold reservoir 12 may include a container 24 with an open end 26 suitable for receiving a lid 28. The container and the lid may be components of the control unit. The cold reservoir may be dimensioned to hold virtually any volume of fluid, and is shown as a 4.2 Liter receptacle. Of course, smaller cold reservoirs may be used, for example, when increased portability is desired, and larger cold reservoirs may be used when, for example, increased capacity is desired.

The temperature of the cold reservoir may be controlled by various mechanisms. In some embodiments, the cold reservoir is adapted to receive ice that may melt in the cold reservoir, and thus decrease the temperature of the fluid in the cold reservoir. As shown in FIG. 1, container 24 has a large open end 26 that is suitable for easily receiving ice. In some embodiments, the cold reservoir may include a cooler for cooling the fluid held in the cold reservoir. Such a cooler may include a compressor and a refrigerant, or similar cooling mechanism. It is within the scope of the invention, however, to use virtually any other suitable method for cooling the fluid held in cold reservoir 12. The cold reservoir may include insulation to limit heat transfer between the fluid held by the cold reservoir and the external environment.

The minimum temperature of the fluid in cold reservoir 12 is usually limited to approximately 32 to 45 degrees Fahrenheit, although such a limitation is not necessary. In particular, it has been found that a temperature of about 35 to 42 degrees Fahrenheit is an appropriate minimum temperature. Although water is usually used as the fluid, it is within the scope of the invention to use other suitable fluids. Such fluids may be selected for particular applications based on their specific heat, viscosity, freezing point, etc.

Contrast therapy system 10 may include an intake 32 for drawing fluid from the cold reservoir. The drawn fluid may pass through a fluid path 34 between cold reservoir 12 and mixing valve 16, as is schematically shown in FIG. 1. Fluid path 34, as well as other fluid paths described herein, may utilize ⅛ inch flexible tubing, or may alternatively implement another suitable fluid transport mechanism. For example, some or all of the fluid paths may alternatively be defined by inflexible fluid conduits. The fluid paths, or other fluid channels such as intake 32, may include filters, flow restrictors, and/or check valves. Filters may help prevent flow blockages resulting from jammed ice or other substances, and check valves may be used to prevent backflow in the system. The rate of fluid flow may be at least partially controlled by flow restrictors.

Hot reservoir 14 is designed to hold a relatively hot fluid, which may be passed to a mixing valve and eventually to a therapy pad. Fluid in the hot reservoir may be heated by a heater 36, which may be positioned adjacent the hot reservoir, or may be incorporated into the hot reservoir. The hot reservoir may be dimensioned to hold virtually any volume of fluid, and is shown dimensioned to hold a volume of approximately 20 to 30 cubic centimeters. It should be understood that the hot reservoir may be smaller or larger, depending on the desired use and the other components of the contrast therapy system.

Heater 36 may be configured so as to achieve a suitable balance of power consumption and heat generation. It has been found that a heater of approximately 280 Watts is appropriate for heating a volume of approximately 20 to 30 cubic centimeters under normal conditions. It should be understood that more powerful and less powerful heaters may be used. Similarly, more than one heater or type of heater may be used.

The flow rate of fluid through the hot reservoir may correspond to the temperature of treatment being applied, with greater flow rates occurring during hotter treatments. During some hot treatments, heater 36 may have limited time to increase the temperature of the fluid because the fluid quickly passes through the hot reservoir, and thus, the heater should be powered so as to increase the temperature a desired amount within that constrained timeframe. However, the heater does not need to completely heat the fluid from a minimum temperature to a maximum temperature in such a timeframe, although it is within the scope of the invention to do so. The hot reservoir receives fluid from the therapy pad, and when a hot treatment is being applied, the return fluid may already be partially heated, decreasing the magnitude of heating required from heater 36. Thus, the net temperature of the fluid may incrementally increase as it repeatedly circulates through the hot reservoir. Nevertheless, a more powerful heater may increase the rate fluid increases temperature in the hot reservoir and/or the maximum temperature of the fluid, thus decreasing the time required to change from a cold treatment to a hot treatment. The maximum temperature of the fluid in hot reservoir 14 is usually limited to approximately 100 to 110 degrees Fahrenheit, although such a limitation is not required. In particular, it has been found that a temperature of about 105 degrees Fahrenheit is appropriate.

As illustrated in FIGS. 2 and 3, hot reservoir 14 receives fluid via a fluid path 38 coming from a bulkhead input 40. As described below, bulkhead input 40 receives fluid returning from the therapy pad. The returning fluid may be directed so that fluid may go to at least one of the hot reservoir, via fluid path 38, and the cold reservoir, via a return 52. In some embodiments, the hot reservoir may be housed within lid 28, which may be securely fit to open end 26 of container 24. Heater 36 may be controlled by an internal control system, external control system, or no control system whatsoever. If present, a control system may regulate the maximum temperature of fluid in the hot reservoir, for example. Such a control system may also be designed to maximize heating efficiency to limit energy requirements.

Mixing Valve

Contrast therapy system 10 includes a mixing valve 16 for receiving a selected ratio of the hot and cold fluids from the hot and cold reservoirs. The mixing valve is operable to deliver a therapy fluid with a therapy temperature that is determined by the selected ratio. In other words, mixing valve 16 may adjustably control the amount of hot fluid from the hot reservoir and the amount of cold fluid from the cold reservoir that mix together. The ratio may be 100% hot fluid from the hot reservoir, in which case the resulting therapy fluid would have a therapy temperature substantially equal to the temperature of fluid leaving the hot reservoir (maximum temperature). The ratio may alternatively be 100% cold fluid from the cold reservoir, in which case the resulting therapy fluid would have a therapy temperature substantially equal to the temperature of fluid leaving the cold reservoir (minimum temperature). Any temperature in between the maximum and minimum temperature may be achieved by adjusting the ratio.

The mixing valve is linked to the cold reservoir and the hot reservoir by respective fluid paths 34 and 42. In some embodiments, one or both of fluid paths 34 and 42 may include a pump, although no pump is required. The mixing valve outputs therapy fluid to a fluid path 44 that leads to the bulkhead output 46, and eventually to therapy pad 22. A pump may be included between the mixing valve and the therapy pad, as shown in FIGS. 2 and 3 and described below. As with the other fluid paths of the contrast therapy system, these fluid paths may include flow restrictors, check valves, filters, overpressure switches, and/or other components. For example, check valve 31 and over pressure switch 33 are illustrated in FIG. 3. The flow paths may include flexible rubber tubing that is approximately ⅛ inch in diameter.

As shown in FIG. 1, the mixing valve may be controlled by a dial 48 that adjusts the ratio of hot and cold fluids delivered from the mixing valve. The dial may be associated with indicia 50 that indicate a relative magnitude of a desired therapy temperature. For example, indicia 50 may include a series of icons representing relative temperatures. A large red dot may represent the hottest therapy temperature, with red dots decreasing in size representing decreasing temperatures. Similarly, a large blue dot may represent the coldest therapy temperature, with blue dots decreasing in size representing increasing temperatures. A dial positioned to point to the large red dot may correspond to a mixing valve position that yields a ratio of 100% hot fluid. As the dial is turned through the progressively smaller red dots, and then through the progressively larger blue dots, the ratio may yield a therapy fluid with a continually increasing percentage of cold fluid.

In some embodiments, the contrast therapy system may include a thermostat that automatically selects the ratio of hot and cold fluids delivered from the mixing valve. For example, the thermostat may be designed to receive manual input of a desired therapy temperature, and adjust the mixing valve to yield a therapy fluid with that temperature. Accordingly, the thermostat may include a temperature measuring device (not shown), such as a thermistor, thermometer, thermocouple, etc. The temperature measuring device may monitor the temperature of the therapy fluid as the thermostat adjusts the mixing valve to yield the desired therapy temperature. The temperature measuring device may cooperate with a temperature display to present the temperature of the therapy fluid. The thermostat may be programmable to automatically change the therapy temperature at a desired time or event by adjusting the ratio of hot and cold fluids delivered from the mixing valve. For example, the thermostat may be programmed to provide alternating hot therapies that last for five minutes at 105 degrees Fahrenheit and cold therapies that last for 5 minutes at 40 degrees Fahrenheit. It should be understood that the thermostat may be programmed for therapies of different durations and/or temperatures.

As shown in FIGS. 2 and 3, contrast therapy system 10 may include a pump 18 for circulating fluid through the system. As illustrated, the pump interposes the mixing valve and the bulkhead output, although the pump may be positioned elsewhere. Similarly, more than one pump may be utilized. As is shown, the pump may be integrated into the lid of the control system. The pump may be powered according to the desired application, and a 4 Watt pump capable of pumping 300 cubic centimeters of fluid per minute has been found to be suitable. The pump may be a reciprocating pump, a rotary pump, or virtually any other suitable pump.

In some embodiments, the pump may be configured to pulse the therapy fluid through the therapy pad. Such a pulsing action may be translated into a therapeutic massage via the therapy pad. As the pulsing fluid circulates through the therapy pad, the therapy pad may vibrate. Pumps designed to pulse fluid may be further enabled to adjust the relative magnitude of the pulsing to correspond to different intensities of therapeutic massages. The relative intensity may be automatically, or manually, coordinated to correspond to a particular temperature of treatment. For example, a vigorous massage may be applied during a hot treatment while a milder massage is applied during a subsequent cold treatment.

Fluidic Coupling Assembly

Figure 4:
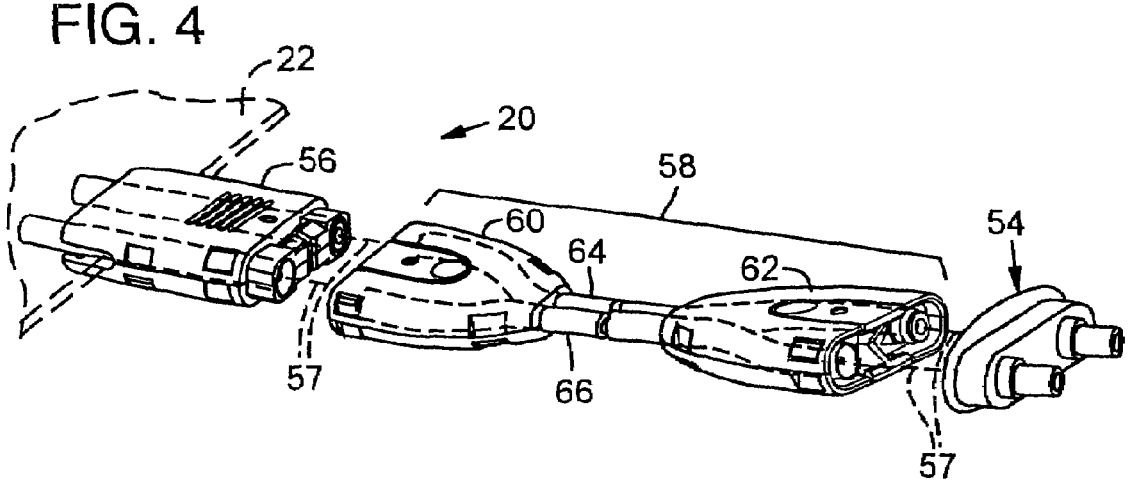
FIG. 4 is an isometric view of a fluidic coupling assembly in accordance with an embodiment of the present invention.

Contrast therapy system 10 may include a fluidic coupling assembly 20 to selectively couple and decouple the mixing valve and the therapy pad. As shown in FIG. 4, the fluidic coupling assembly usually includes a bulkhead 54, which is in fluid communication with the mixing valve, a wrap connector 56 in fluid communication with therapy pad 22, and a reversible tubing assembly 58 for linking the bulkhead to the wrap connector. The reversible tubing assembly includes a first tube-set connector 60 and a second tube-set connector 62 that are functionally equivalent to one another. First tube-set connector 60 and second tube-set connector 62 are linked by fluid paths 64 and 66.

Bulkhead 54, first tube-set connector 60, second tube-set connector 62, and wrap connector 56 each include one male valve and one female valve, which are configured to mate with a corresponding female and male valve, for example, as shown by dotted lines 57 in FIG. 4. The bulkhead and the wrap connector are each configured to releasably receive either the first tube-set connector or the second tube-set connector. Therefore, tubing assembly 58 is completely reversible. For example, the bulkhead and the first tube-set connector may be coupled so that the bulkhead's male valve mates with the first tube-set connector's female valve, and the bulkhead's female valve mates with the first tube-set connector's male valve. Likewise, the wrap connector and the second tube-set connector may be coupled so that the wrap connector's male valve mates with the second tube-set connector's female valve, and the wrap connector's female valve mates with the second tube-set connector's male valve. Because the tubing assembly is reversible, the above described connection may be reversed. For example, if the first tube-set connector is connected to the bulkhead, the second tube-set connector is available for connection to the wrap connector, but if the second tube-set connector is connected to the bulkhead, the first tube-set connector is available for connection to the wrap connector. In either case, such arrangements permit fluid to flow from the control unit to the therapy pad, and then return back to the control unit.

The male and female valve of each of the above described components are equally spaced from one another. Therefore, male and female valves from one component may align with female and male valves from a corresponding component. Furthermore, bulkhead 54 is complementarily configured relative to both the first and second tube-set connectors to facilitate securing either the first tube-set connector or the second tube-set connector to the bulkhead. Similarly, either the first tube-set connector or the second tube-set connector may be secured to the wrap connector. The male and female valves are designed to prevent fluid flow unless they are mated with one another, thus limiting leakage when disconnecting the reversible tubing assembly from the control unit and/or the therapy pad.

The configuration of the fluidic coupling assembly facilitates easy connection and disconnection of a plurality of control units, tubing assemblies, and/or therapy pads. For example, the same control unit may be used with a variety of different therapy pads, which may be individually configured to treat different areas of a recipients body. Similarly, a single therapy pad may be used with a variety of different control units, for example, when a recipient moves from one therapy location to another. The fluidic coupling assembly facilitates quick and easy coupling and decoupling, and the leak reducing male and female valves help limit spillage during such coupling and decoupling.

Therapy Pad

Figure 5:
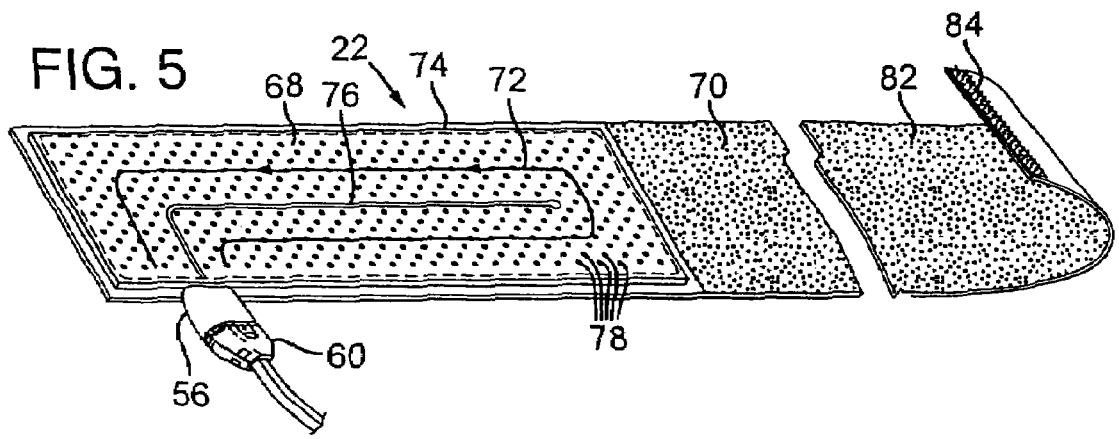
FIG. 5 is an isometric view of a contrast therapy pad in accordance with an embodiment of the present invention.

FIG. 5 shows therapy pad 22 apart from the remainder of the contrast therapy system. As described above, the therapy pad may be easily coupled and decoupled from the reversible tubing assembly, which allows various different therapy pads to be used with the same control unit. Each therapy pad is designed to receive therapy fluid from the mixing valve, such as through the fluidic coupling assembly, and return the therapy fluid to at least one of the hot reservoir and the cold reservoir (as shown schematically in FIG. 2). The therapy pad returns fluid to the control unit, and the returned fluid may be recirculated. Depending on the type of therapy being applied, returned fluid may be heated and/or cooled at the control unit. The contrast therapy system may include a return valve that selectively directs return fluid to the hot reservoir and/or the cold reservoir, or the return fluid may be allowed to naturally flow to the lower pressure region.

Figure 6:
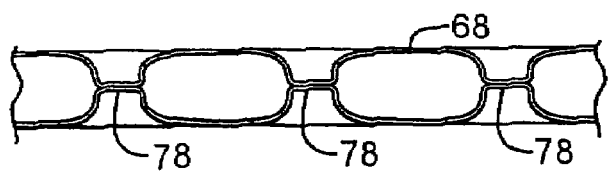
FIG. 6 is a cross-sectional view of a portion of the contrast therapy pad of FIG. 5.

In some embodiments, the therapy pad includes an active thermal exchange bladder 68 and an elastic wrap 70 that is connected to the thermal exchange bladder. The thermal exchange bladder may include a flexible membrane of opposing faces that are welded together to define a channel system for directing the flow of therapy fluid along a desired fluid path 72 within the thermal exchange bladder. For example, the faces are usually welded along a common outer perimeter 74, sealing the faces together. A division weld 76 may direct fluid through a substantial portion of the pad before returning to the control unit. The thermal exchange bladder may also include a plurality of intermittent welds 78, that limit inflation of the bladder, as shown in FIG. 6, which is a cross-sectional view of a portion of the exchange bladder.

The thermal exchange bladder facilitates thermal exchange between a therapy site and the therapy fluid. For example, when a cold therapy is administered, heat from a recipient's body may heat the therapy fluid, which in turn cools the therapy site. Similarly, when a hot therapy is administered, the therapy fluid may transfer heat to the therapy site. The therapy may be enhanced by moistening the bladder to provide a moist therapy. Furthermore, the fluid may also be pulsed through the bladder, adding a therapeutic massage aspect to the treatment.

In the illustrated embodiment, therapy pad 22 is dimensioned to hold approximately 150 cubic centimeters of fluid. However, the volume of the therapy pad may be controlled by changing the size of the therapy pad, and/or the amount of inflation the intern littent welds allow. Furthermore, the therapy pad may be constructed from an at least partially elastic material, such as urethane, which may permit the volume to change in response to the pressure of fluid within the bladder. In some embodiments, the bladder may include a less elastic material that helps prevent stretching, such as a vinyl/urethane blend.

As shown in FIG. 5, fluid may enter the bladder at wrap connector 56, flow around the division weld and the intermittent welds, and leave the bladder at the wrap connector. It is within the scope of the invention to reconfigure the bladder to accommodate different flow paths. For example, the division weld, or plural division welds, may be used to direct the fluid through a series of switchbacks before returning to the output of the wrap connector. Small breaks may be included in the division weld to permit alternative flow paths if a primary flow path is blocked.

Elastic wrap 70 is shown connected to the thermal exchange bladder. The elastic wrap may be configured to adjustably wrap around the thermal exchange bladder and compress the thermal exchange bladder around a therapy site. Compression helps induce contact of the bladder with the therapy site, which may promote efficient and even thermal transfer. Furthermore, the wrap is a compressive element in and of itself. When used in conjunction with the bladder, it keeps the bladder in contact with the therapy site, and it may also help reduce swelling through its own inherent compressibility. The wrap is continuously adjustable, meaning it may be repeatedly tightened and loosened to various levels of compression, as shown in FIG. 7. The wrap may be used in tandem with the bladder to wrap a therapy site in a variety of ways, thus providing extreme flexibility in the types of treatments that may be administered to a wide range of different therapy sites.

Figure 7A:
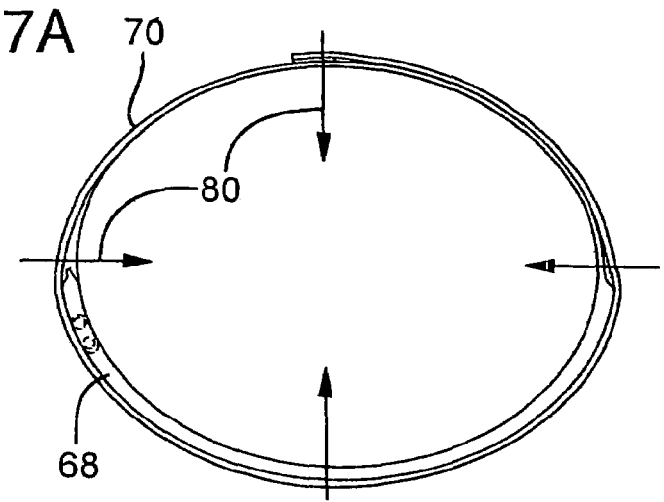
FIG. 7A is a cross-sectional view of the therapy pad of FIG. 7 wrapped around the therapy recipient.

Wrap 70 is elastic; it may be stretched and naturally return to an unstretched disposition. When stretched, the wrap is at an increased tension, which may be used to compress a therapy pad around a therapy site, as shown in FIG. 7A. Force vectors 80 schematically represent the compressive force resulting from the wrap. The magnitude of the compressive force may be selected by adjusting the amount the wrap is stretched. As the wrap is increasingly stretched around a therapy site, the compressive force the wrap applies increases. Similarly, the wrap may be loosened, decreasing the magnitude of the compressive force. The amount of elasticity a particular wrap has may be selected according to a desired application, or range of applications. In some embodiments, the wraps are designed to stretch to approximately 150%-200% of their unstretched length, however less elastic and more elastic wraps may be used. The wraps may be variously sized, and are usually at least as long as their corresponding bladder when unstretched. As illustrated in FIG. 5, the unstretched wrap is six times as long (54 inches) as the bladder (18 inches). Because of the elastic configuration of the wrap, wrapping techniques known to physical therapists, physical trainers, and sports physicians may be used in conjunction with the therapy pad to achieve a wide variety of therapeutic benefits.

As shown in FIG. 5, elastic wrap 70 is permanently connected to thermal exchange bladder 68. The wrap may be connected by stitching, an adhesive, and/or another suitable fastener. In some embodiments, the bladder is connected to the wrap via an optional mesh envelope, shown in dashed lines at 69. In such embodiments, the envelope may be permanently connected to the wrap, and the bladder may be selectively positioned within the mesh envelope. The mesh envelope may include a fastening face configured to selectively fasten with a complimentary fastener of the wrap. The wrap may alternatively be removably connected to the bladder, such as by hook and loop connectors. By permanently connecting the wrap to the bladder, such as by stitching or configuring an envelope to securely hold the bladder relative to the wrap, the wrap and the bladder may cooperate to provide a compressive force, as described herein. Furthermore, the combination has proven to be much easier to apply than separated therapy pads and wraps, and thus is more versatile.

The wrap usually includes a surface of loops 82 that are adapted to detachably receive complementary hooks 84. The hooks and loops are positioned, so that the hooks may engage the loops when the wrap is wrapped around a therapy site, as shown in FIGS. 7 and 7A. The wrap may be adjusted to a desired tension and a corresponding level of compressive force that may be fixed by engaging the hooks and the loops together. The hooks and loops may subsequently be disengaged, so that the tension may be adjusted, for instance, and reengaged at will. In some embodiments, a wrap lock may alternatively be used to secure the wrap.

In some embodiments, the therapy pads may be constructed with disposable materials. For example, pads configured for a single use may be constructed from disposable materials, which are usually less expensive than reusable materials. Disposable therapy pads may be particularly useful in emergency, trauma, or post surgery situations, in which a therapy recipient may bleed onto the therapy pad. The ability to control the temperature of the therapy pad, either reusable or disposable, may increase the pad's effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Wraps may alternatively be configured to be washable, such as by a laundry machine, and therefore may be sanitarily reused.

The thermal exchange bladder may be sized and shaped according to a particular range of applications. For example, a 6 inch by 18 inch bladder (as shown at 22 in FIG. 5) may be useful in treating backs, legs, arms, shoulders, and other therapy sites. Although the versatile configuration of therapy pad 22 may be used for virtually any therapy site, other therapy pads may be configured to even better accommodate particular therapy sites. For example, a 2 inch by 18 inch bladder 86, as shown in FIG. 8, may be particularly useful for treating smaller therapy sites, such as hands, wrists, feet, ankles, etc. Similarly, a shoulder therapy pad may be designed to intimately engage a shoulder therapy site, thus providing comfortable and improved treatment. A jaw therapy pad, which is useful in treating the facial area, may be designed to comfortably wrap around a head, while positioning a bladder in contact with at least one side of a jaw. It should be understood that the above therapy pads are provided as examples, and other therapy pads may also be used. Furthermore, each therapy pad may include a suitable elastic wrap and/or other fastening mechanism.

The therapy system may be used to treat a wide range of conditions, including injured muscles, bones, joints, tendons, ligaments etc. Furthermore, other conditions may be treated, such as mastitis or breasts that are sore from menstruation. The therapy system may also be used as a preventative remedy, for example the therapy system may be used during child birth to help alleviate discomfort during labor as well as help minimize resulting soreness and/or discomfort. For example, providing a cold treatment to a recipient's back during child birth may help cool the recipient, thus alleviating immediate discomfort, as well as subsequent soreness.

Contrast therapy system 10 may include a power supply, such as 92 of FIG. 3, for providing power to various components of the system, such as a heater, cooler, pump, thermostat, display, etc. In some embodiments, the power supply may provide alternating current, while in other embodiments, the power supply may provide direct current. Some embodiments may be configured to operate with either AC or DC power. For example, the contrast therapy system may include a DC heater and pump designed to draw power from either a battery or an electrical outlet via an AC/DC converter. Batteries used to power the contrast therapy system may be externally connected to the system, and/or housed within the system. The contrast therapy system may be powered from alternative power sources as well.

Method of Administering Contrast of Thermal Therapy

FIG. 9 shows, generally at 100, a method of administering contrast therapy to a therapy recipient. Method 100 includes, at 102, providing a volume of a relatively hot fluid. As explained above, a fluid may be received by a hot reservoir, where it may be heated by a heater. The relatively hot fluid may be virtually any temperature, with temperatures of approximately 100 to 105 degrees Fahrenheit being suitable for many applications. The method further includes, at 104, providing a volume of a relatively cold fluid. Fluid may be received by a cold reservoir, where it may be cooled. In some embodiments, an ice slurry is used to cool fluid passing through the cold reservoir, and in some embodiments a cooler is used. The cold fluid may be virtually any temperature (cooler than the hot fluid), with temperatures of approximately 32 to 45 degrees Fahrenheit being suitable for many applications.

At 106, the method includes selecting relative amounts of the hot and cold fluids to mix as a therapy fluid with a desired initial therapy temperature. A mixture of hot and cold fluids with a specific ratio may be selected with a mixing valve, or similar mechanism, that is configured to receive the hot and cold fluids, and pass the mixture of the hot and cold fluids as a therapy fluid. The ratio of hot to cold fluid in the therapy fluid may range from 100% hot fluid to 100% cold fluid, as well as any intermediate ratio. The temperature of the therapy fluid corresponds to the ratio of hot and cold fluids mixed, with greater percentages of hot fluid resulting in higher temperatures, and greater percentages of cold fluid resulting in cooler temperatures. The therapy fluid's maximum temperature is approximately the temperature of the hot fluid, and is achieved by selecting a ratio of all hot fluid and no cold fluid. Similarly, the therapy fluid's minimum temperature is approximately the temperature of the cold fluid, and is achieved by selecting a ratio of all cold fluid and no hot fluid.

As shown at 108, the method further includes circulating the therapy fluid with the initial therapy temperature through a therapy pad. The therapy fluid may be circulated in a pulsing stream, so as to impart a vibration that is useful in providing a therapeutic massage. Of course, the flow may instead be smooth. At 110, the method includes applying the therapy pad to the therapy recipient. The temperature of the therapy fluid may be translated through the therapy pad to the therapy recipient. For example, if the initial temperature of the therapy fluid is relatively hot, for instance 105 degrees Fahrenheit, the therapy pad may be used to heat a therapy site on the therapy recipient. Similarly, a therapy fluid with a relatively cold therapy temperature, such as 40 degrees Fahrenheit, may be used to cool a therapy site. The pad may be applied to a therapy recipient by using an integrated elastic wrap to compress the therapy pad around a therapy site, which may add to the benefits of the treatment.

The method further includes, at 112, returning the therapy fluid to at least one of the volume of hot fluid and the volume of cold fluid. Returning the therapy fluid to either or both of the volumes of hot and cold fluids allows the therapy fluid to be recycled. The returned therapy fluid may then be heated and/or cooled, and eventually may be recirculated to the therapy pad. In this manner, a limited volume of fluid in a system may be used to provide an ongoing therapy. The fluid may be repeatedly heated and/or cooled, and thus the character of the treatment may be continually changed.

As shown at 114, the method may also include selecting relative amounts of the hot and cold fluids to mix as a therapy fluid with a desired contrast therapy temperature different than the initial therapy temperature. By changing the relative amounts of hot and cold fluids, the resulting temperature of the therapy fluid may be changed, which changes the therapy received by the therapy recipient. It is within the scope of the invention to make such temperature changes quickly, such as in under a minute, which may result in an average temperature change greater than 1 degree Fahrenheit per second. At 116, the method may further include circulating the therapy fluid with the contrast therapy temperature through the therapy pad. Circulating the therapy fluid with the contrast therapy temperature allows the therapy recipient to experience a cold treatment immediately after a hot treatment or a hot treatment immediately after a cold treatment. It should be understood that the period of change between respective treatments is ideally very small, such as under one minute. This process may be repeated one or more times, and each time the relative amounts of hot and cold fluids may be selected to result in a desired therapy temperature.

Mixing Valve Assembly

Mixing valve assembly 1601 selectively combines fluid received from the cold reservoir 12 and hot reservoir 10, and passes the combined fluid to the therapy pad 22 as a therapy fluid at a selected therapy temperature. As noted above, the mixing valve assemble 1601 is capable of controlling the temperature of the therapy fluid (hereinafter "therapy temperature"), changing between relatively high and low temperatures in a short period of time. The mixing valve assembly 1601 may control the therapy temperature by incrementally controlling the amount of relatively high temperature fluid received from the hot reservoir 10 and the amount of relatively low temperature fluid received from the cold reservoir 12 that mix together.

Figure 11:
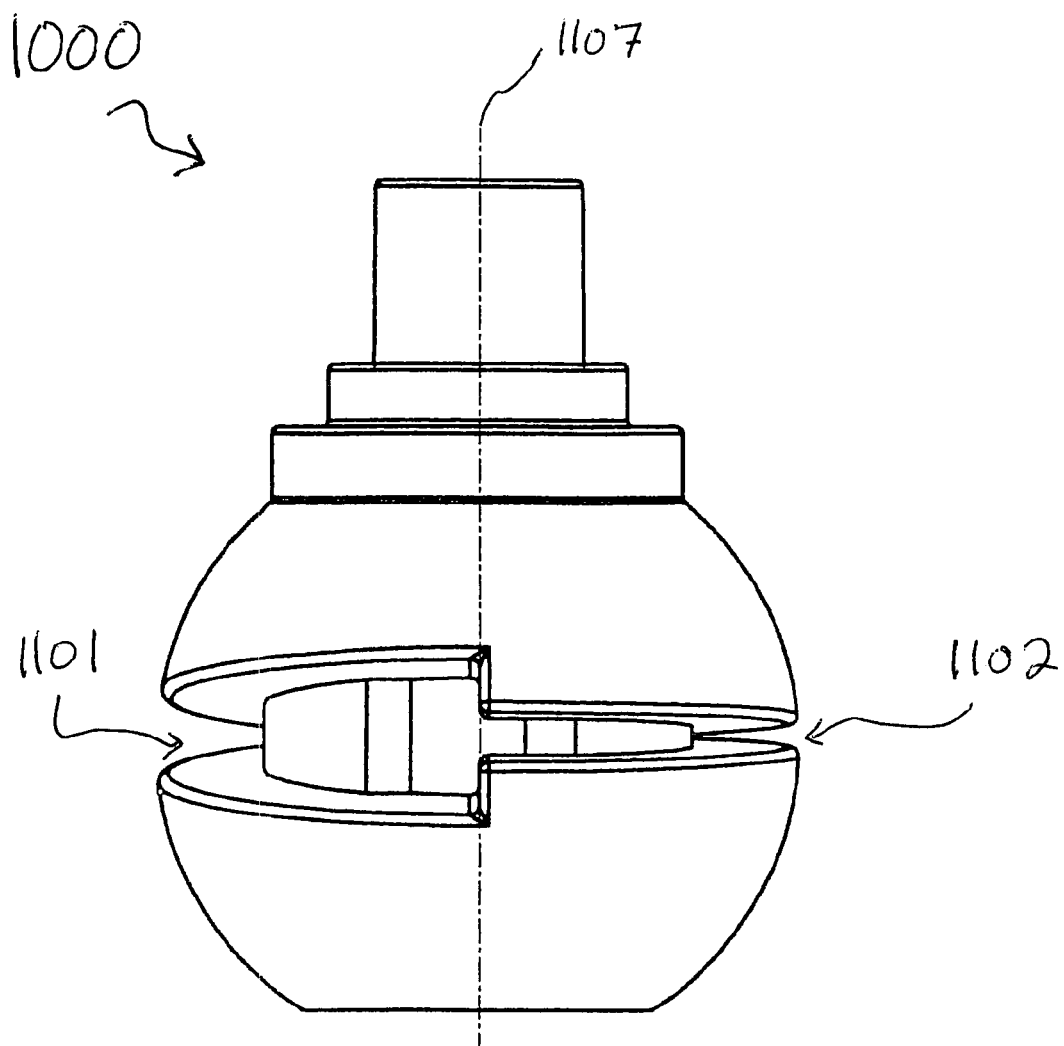
FIG. 11 is a plan view of a ball element in accordance with an embodiment of the present invention.
Figure 12A:
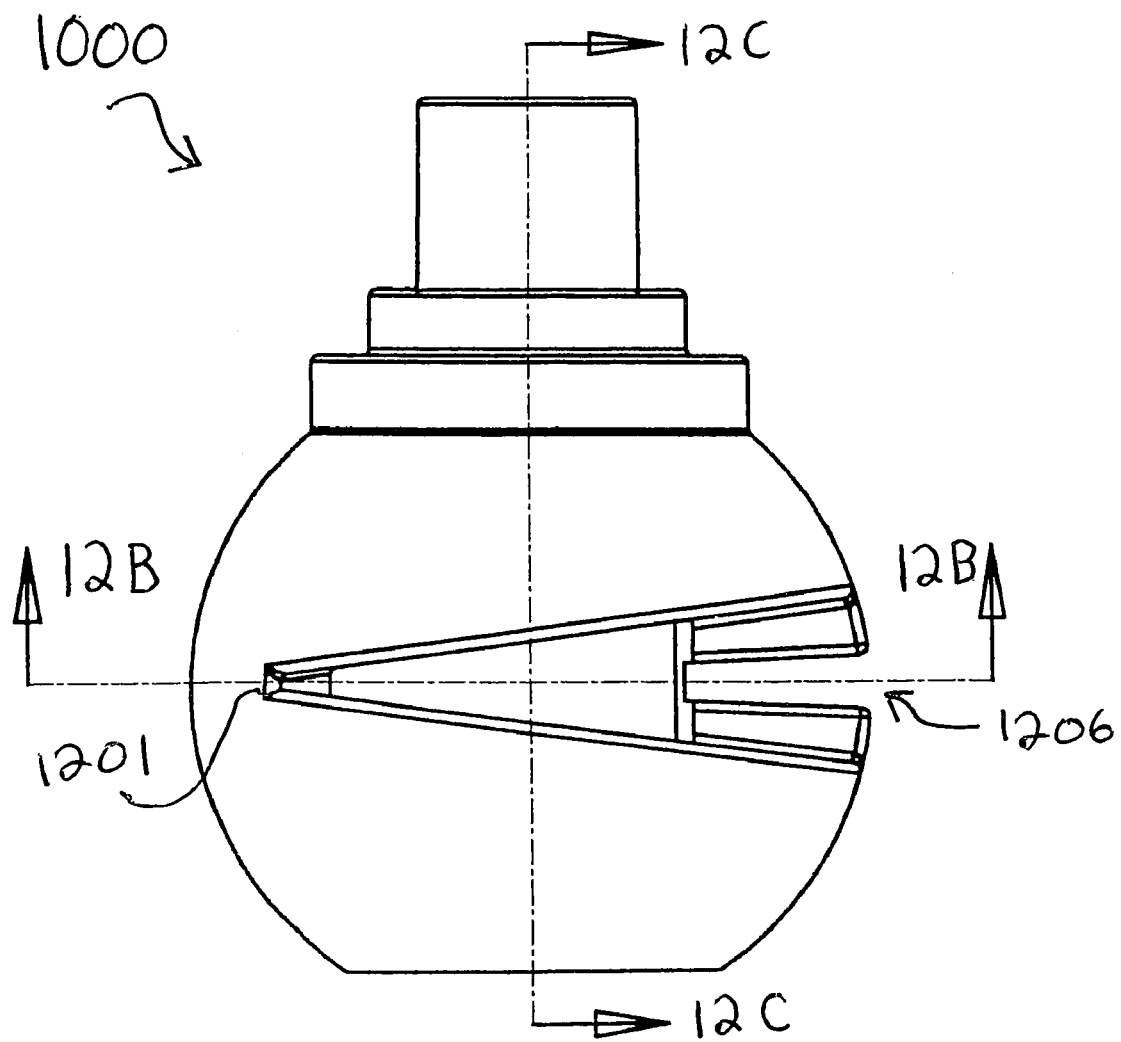
FIG. 12A is a plan view of a ball element in accordance with an embodiment of the present invention indicating cross sectional views 12A and 12B.

Referring now to FIG. 10, incremental temperature control is achieved by incorporating the ball element 1000 of the instant invention into the mixing valve assembly 1601. As shown in FIGS. 11 and 12A, a preferred embodiment of ball element 1000 is characterized by a first inlet 1102 and a second inlet 1101. Any number of inlets may be used depending upon the particular application.

In a preferred embodiment, mixing valve assembly 1601 may advantageously be configured to provide relatively high temperature fluid from the hot reservoir 10 to the first (or high temperature) inlet 1102, and relatively low temperature fluid from the cold reservoir 12 to the second (or low temperature) inlet 1101. Incremental control of the therapy temperature is achieved by adjusting the rotational position of the ball element 1000 within the mixing valve assembly 1601. The ball element 1000 may be rotated about its axis of rotation 1107 to the desired position.

Figure 12B:
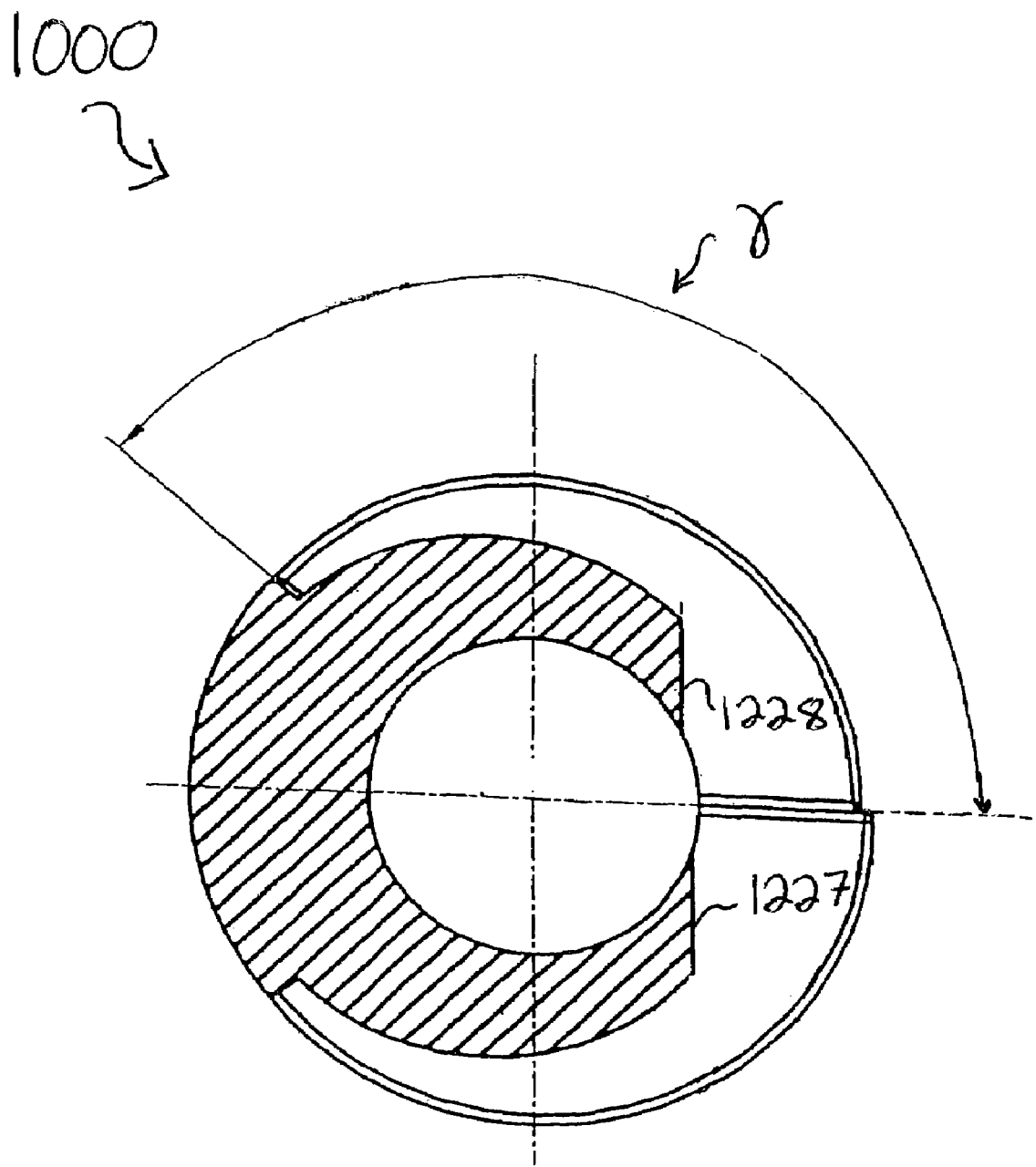
FIG. 12B is a cross-sectional view of a portion of the ball element of FIG. 12.
Figure 12C:
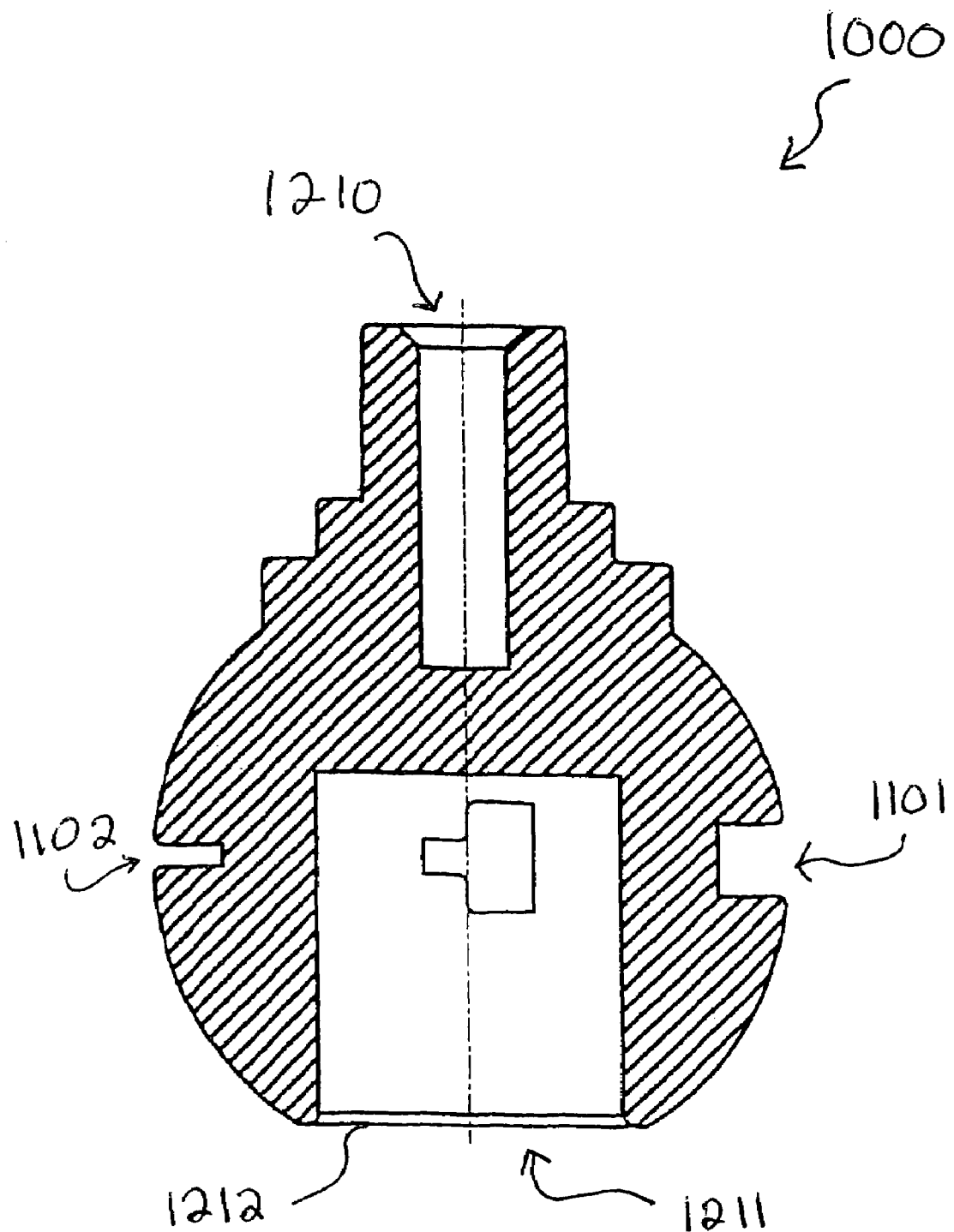
FIG. 12C is a cross-sectional view of a portion of the ball element of FIG. 12.
Figure 13:
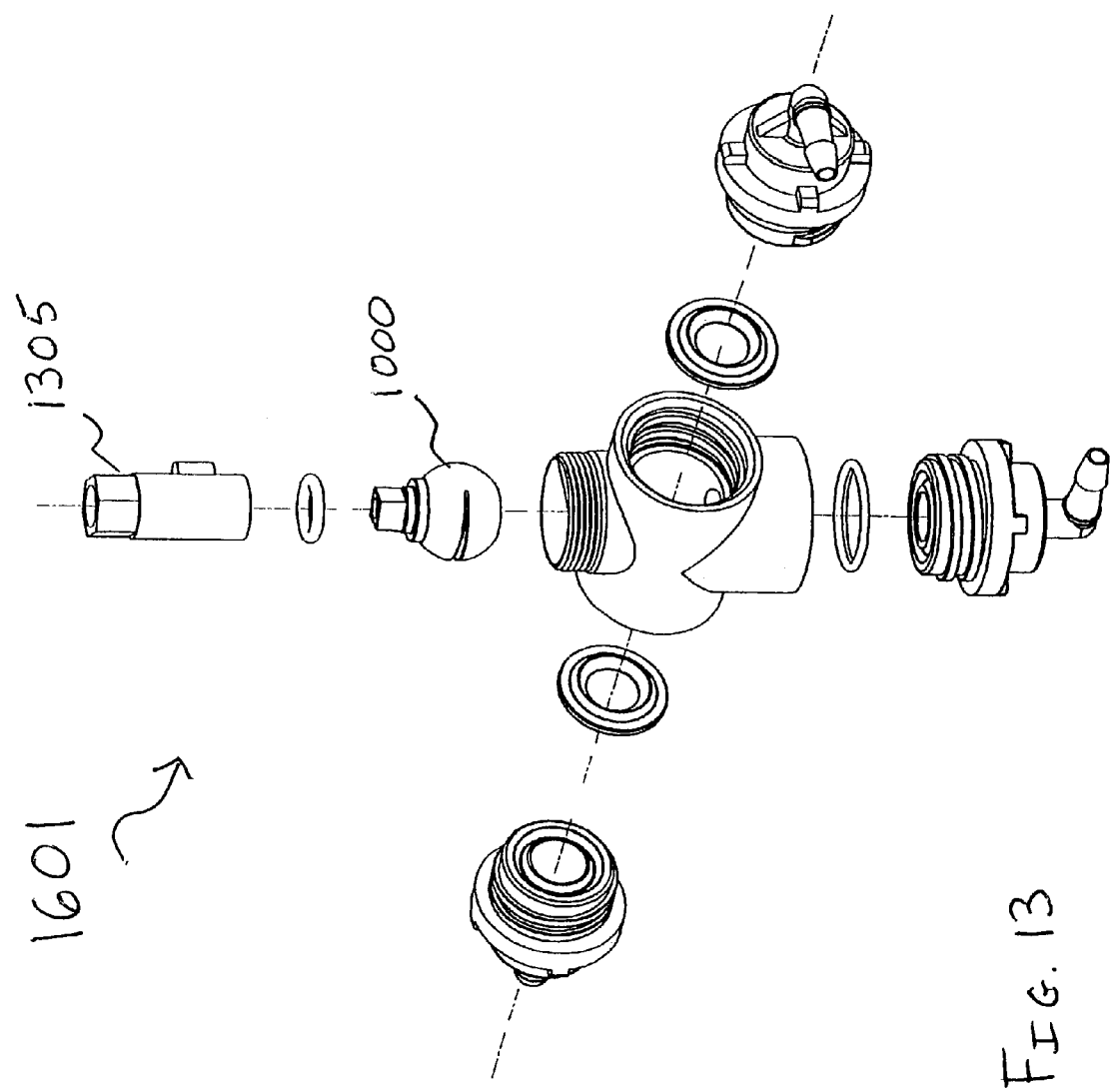
FIG. 13 is a schematic view of a mixing valve assembly in accordance with an embodiment of the present invention.

Referring now to FIG. 12C, first inlet 1102 and second inlet 1101 are in fluid communication with mixing chamber 1211 which, in turn, is in fluid communication with outlet 1212. Fluid may flow from outlet 1212 through mixing valve assembly 1601 to a selected therapy device. Adjusting the rotational position of the ball element 1000, in turn, adjusts the ratio of relatively high and low temperature fluids which pass into the mixing chamber 1211. As a result, the therapy temperature is incrementally controlled through incremental rotation of the ball element 1000 about its axis 1107. A control stem 1305 may be attached at the ball assembly actuator receptacle 1210 to effectively control rotational positioning. The control stem may advantageously be connected to a dial 48 which allows the user to select therapy temperature. Or, alternatively, the stem may automatically be controlled via a servo or some other automatic actuating device.

The selected ratio of relatively high temperature fluid and relatively low temperature fluid may be 100% hot fluid from the hot reservoir 10 in which case the resulting therapy fluid would have a therapy temperature substantially equal to the temperature of the fluid leaving the hot reservoir 10. This would define a high temperature maximum for the therapy fluid exiting the outlet 1212 of the ball element 1000. The selected ration may alternatively be 100% cold fluid from the cold fluid reservoir 12 in which case the resulting therapy fluid would have a therapy temperature substantially equal to the temperature of the fluid leaving the cold reservoir 12. This would define a low temperature minimum for the therapy fluid. Any temperature between the maximum and minimum may be achieved by incrementally adjusting the rotational position of the ball element according to the present invention.

Preferably, fluid passes from the hot reservoir 10 through the first inlet 1102 and into the mixing chamber 1211. If the selected ratio is 100% from the hot reservoir 10, then the fluid passes through the outlet 1212 to a selected therapy device at substantially the maximum therapy temperature. Similarly, if the selected ratio is 100% from the cold fluid reservoir 12, fluid passes through the second inlet 1101, through the mixing chamber 1211 and outlet 1212 to the selected therapy device at substantially the minimum therapy temperature. Advantageously, the selected ratio may be chosen to give any temperature from minimum to maximum therapy temperature.

By incrementally adjusting the rotational position of the ball 1000, relatively high and low temperature fluids may pass through their respective inlets at the selected ratio. The fluids are mixed in the mixing chamber 1211 and pass through the outlet 1212 at the desired therapy temperature. The present invention gives linear control over therapy temperature changes over the entire range of possible therapy temperatures. The instant ball element allows the user to progress through a substantially linear progression of therapy temperature increases (or decreases) from minimum to maximum temperature. As a result, a linear outlet therapy temperature profile may be achieved. Of course, any desired temperature profile (including linear or non-linear) may be achieved using the instant invention.

Known balls do not afford the user linear temperature control over the range of therapy temperatures. Preferably, therapy temperatures range from a minimum of about 40° F. to a maximum of about 105° F. Temperatures below the minimum or above the maximum may cause tissue necrosis or other tissue damage. As shown in FIG. 14, known balls only offer linear temperature control over a very small range of temperatures near the minimum and maximum therapy temperatures.

As can be seen in Table 1, below, therapy fluid temperature near the minimum is quickly overwhelmed by the introduction of high temperature fluid from the hot reservoir 10. The user is afforded no linear control over therapy temperature over the majority of the given temperature range. The practical effect is that the user may select only a minimum, maximum and intermediate temperature.

TABLE 1

| POSITION THE OF KNOB | TEMPERATURE (° F.) | FLOW RATE (ml/min) | PRESSURE (Psi) | INTERVAL OF SAMPLING |
|---|---|---|---|---|
| 1 | 44 | 193 | 15 | 5 mins |
| 2 | 53 | 210 | 16 | 5 mins |
| 3 | 55 | 220 | 16.7 | 5 mins |
| 4 | 59 | 208 | 16.7 | 5 mins |
| 5 | 64 | 215 | 16 | 5 mins |
| 6 | 66 | 213 | 16.4 | 5 mins |
| 7 | 69 | 215 | 14.4 | 5 mins |
| 8 | 71 | 220 | 14 | 5 mins |
| 9 | 76 | 216 | 13.7 | 5 mins |
| 10 | 82 | 210 | 13 | 5 mins |
| 11 | 88 | 202 | 12.6 | 5 mins |
| 12 | 107 | 193 | 10 | 5 mins |

Known balls commonly offer a series of bores or holes which act as inlets for both the relatively low and high temperature fluids. A set of bores for each temperature fluid may range from a relatively small size hole through progressively larger holes to a relatively large size hole. In the example given by Table 1, above, each series of bores offered the same size holes for both the hot and cold fluids.

In the instant invention, the ball is modified by replacing the bores with continuously varying wedge shaped restrictive openings. Table 2, below, is an illustration of the temperature profile of the outlet therapy fluid achieved through the use of the modified ball. The instant wedge shaped inlets give substantially linear temperature control of the outlet therapy temperature profile. The modified ball offers better incremental control of therapy temperature.

TABLE 2

| POSITION OF THE KNOB | TEMPERATURE (° F.) | FLOW RATE (ml/min) | PRESSURE (Psi) | INTERVAL OF SAMPLING |
|---|---|---|---|---|
| 1 | 44 | — | — | 5 mins |
| 2 | 55 | — | — | 5 mins |
| 3 | 57 | — | — | 5 mins |
| 4 | 60 | — | — | 5 mins |
| 5 | 63 | — | — | 5 mins |
| 6 | 64 | — | — | 5 mins |
| 7 | 68 | — | — | 5 mins |
| 8 | 72 | — | — | 5 mins |
| 9 | 77 | — | — | 5 mins |
| 10 | 77 | — | — | 5 mins |
| 11 | 86 | — | — | 5 mins |
| 12 | 105 | — | — | 5 mins |

In a preferred embodiment of the instant invention, interior restrictor walls are added to form inlet chambers at each of inlets 1101 and 1102. When used in conjunction with a relatively hot and a relatively cold input fluid, the ball element is designed to give complete linear temperature control over the entire range of available therapy temperatures. As shown in FIG. 15, the instant ball element 1000 allows the user to incrementally control changes in therapy temperature from minimum therapy temperature to maximum therapy temperature. This provides the advantage of allowing for more effective therapy by enabling users to apply the indicated progression of thermal therapy treatment most effective for addressing the presented injury. There is provided the additional advantage of making the therapy experience more comfortable to the user. As a result, the user is more likely to follow the indicated therapy regimen.

Table 3, below, is an illustration of the progression of temperature changes achieved through the use of the instant ball element 1000 and depicted in FIG. 15. The user is afforded complete linear control over temperature changes for the entire range of allowable therapy temperatures.

TABLE 3

| POSITION OF THE KNOB | TEMPERATURE (° F.) | FLOW RATE (ml/min) | PRESSURE (Psi) | INTERVAL OF SAMPLING |
|---|---|---|---|---|
| 1 | 45 | 266 | 15.7 | 5 mins |
| 2 | 47 | 278 | 17.5 | 5 mins |
| 3 | 53 | 277 | 18.2 | 5 mins |
| 4 | 58 | 282 | 16.8 | 5 mins |
| 5 | 70 | 279 | 14.0 | 5 mins |
| 6 | 75 | 262 | 14.0 | 5 mins |
| 7 | 78 | 266 | 14.3 | 5 mins |
| 8 | 82 | 268 | 14.8 | 5 mins |
| 9 | 87 | 255 | 12.7 | 5 mins |
| 10 | 89 | 238 | 12.5 | 5 mins |
| 11 | 97 | 260 | 12.1 | 5 mins |
| 12 | 105 | 258 | 11.6 | 5 mins |

In a preferred embodiment, the inlets of the ball element 1000 of the instant invention are substantially wedge shaped. The first inlet 1102 and second inlet 1101 are characterized by wide forward edges which meet in a pre-mixing zone 1206. Each inlet tapers to a narrow rear apex as illustrated by the second inlet apex 1201. In a another embodiment, the second inlet 1101 is larger than the first inlet 1102.

Refereeing now to a more preferred embodiment of the ball element 1000 of the instant invention is shown. Said second inlet 1101 is substantially larger than the first inlet 1102. The wide forward edge of the second inlet forms a 15° angle at the surface of the ball element. Whereas, the wide forward edge of the first inlet 1102 forms a 5° angle at the surface of the ball element 1000.

Preferably, the wedge shaped first and second inlets are further characterized by the length of their extension around the circumference of the ball element 1000. As shown in FIG. 12B, each inlet extends from its wide forward edge to its narrow rear apex over an angle γ of 140°.

In a preferred embodiment, the ball element 1000 of the instant invention includes internal restrictor wall elements. The temperature profile achieved with said ball was shown to be substantially linear as shown above in Table 3 and in FIG. 16. Referring now to FIG. 12B, cold restrictor wall 1227 and hot restrictor wall 1228 act to restrict flow of cold and hot fluids respectively. Restrictor walls 1227 and 1228 define a low temperature inlet chamber and a high temperature inlet chamber, respectively. The restrictor walls channel fluid entering the first and second inlet to a pre-mixing area 1106. The fluids then progress to the mixing chamber 1211 where they are mixed to achieve the desired therapy temperature.

The restrictor walls advantageously act in conjunction with the wedge shaped inlets to enhance the ability of the instant ball element 1000 to offer linear control of therapy temperature changes over the range of therapy temperatures. By restricting communication between the hot and cold inlets and first channeling the hot and cold fluids to a pre-mixing area 1106, the restrictor walls enhance the ability of the ball element 1000 to effectuate incremental therapy temperature changes.

Automatic temperature control may be achieved using a servo in conjunction with the thermostat discussed above. For instance, the control stem 1305 may be driven by the servo using a step motor with a home switch, or the like. In this manner, any outlet temperature profile, including a linear outlet temperature profile, may be achieved automatically.

Using automatic control, it may be desirable to tag a lowest possible temperature to avoid the hunting effect, discussed above. The lowest temperature may be tagged at, for instance, 55 degrees Fahrenheit in order to avoid the hunting effect in a broad range of cases. The control may also be tailored to each individual's physiology such that the lowest possible temperature is tagged at the tagged just above the temperature at which the hunting effect is implicated for that individual. In this way, the instant invention automatically affords the user the benefits of cold therapy while avoiding the hunting effect.

Known mixing valves tend to afford the user little temperature control. In general, known valves would afford the user an output therapy temperature that was low, intermediate, or high, with no linear control throughout. As a result, the hunting effect could not be avoided in most cases at the low end, while the most effective cold therapy was not afforded in the intermediate range.

It is also desirable to maintain a constant pressure in the therapy pad to present the user with a comfortable feel at the therapy site. To achieve this, a substantially constant pressure and flow rate must be maintained in the outlet fluid exiting the mixing valve assembly. As discussed above, a pump may be included between the mixing valve and the therapy pad. In this manner, a substantially constant output pressure and flow rate may be achieved. However, if the inlet flow resistance offered by fluid paths 34 and 42 is substantially different, the flow rates of the respective cold and hot fluids will be effected.

In order to maintain the desired linear outlet therapy temperature profile and a constant outlet pressure and flow rate in the presence of differing inlet flow resistances, the size of the wedge shaped inlets must be adjusted accordingly. It has been found that by making the relative size of the inlets proportional the relative magnitude of their respective inlet flow resistances, a linear temperature profile can be achieved while maintaining constant outlet pressure and flow rate. As a result, any system may be modified to achieve a linear temperature profile while maintaining constant outlet pressure and flow rate by tailoring the relative sizes of the inlets proportionally to the respective relative inlet flow resistances. By simply replacing the ball element of the mixing valve assembly of any system with the instant ball element tailored to the particular system, the desired results may be achieved.

The mixing valve assembly 1601 of the instant invention may be used to effectively carry out the method of administering thermal or contrast therapy. As described above, the method 100 includes providing a volume of relatively high temperature (hot) fluid at 102 and a volume of relatively low (cold) temperature fluid at 104. At 106, the method includes selecting relative amounts of hot and cold fluids to mix as a therapy fluid at a desired initial therapy temperature. The method includes circulating the therapy fluid with the initial therapy temperature through a therapy pad at 108. A therapy pad is used for illustrative purposes herein. As disclosed above, the present invention may be used to provide therapy fluid at a selected therapy temperature for any of a variety of temperature therapy devices. The method further includes, at 112, returning the therapy fluid to at least one of the volume of hot fluid and the volume of cold fluid so as to provide a continuous flow of therapy fluid at variously selected therapy temperatures.

As shown at 114, the method may also include selecting relative amounts of the hot and cold fluids to mix as a therapy fluid with a desired thermal or contrast therapy temperature different than the initial therapy temperature. By changing the relative amounts of hot and cold fluids, the resulting temperature of the therapy fluid may be changed, which changes the therapy received by the therapy recipient.

The ball element 1000 of the instant invention allows the therapy recipient to have linear control of the temperature of the therapy fluids over the entire range of available therapy temperatures. Selecting relative amounts of hot and cold fluids to mix as a therapy fluid at 114 is achieved by adjusting the rotational position of the instant ball. The amount of fluid entering the first inlet 1102 and second inlet 1101 is determined by the rotational position of the ball element 1000. This, in turn, determines the therapy temperature of the therapy fluid leaving the mixing chamber 1211 through the outlet 1212 of the ball. The instant invention provides a method for incremental control of therapy fluid temperature received by the therapy recipient.

The present invention can also be practiced with other techniques for providing thermal or contrast therapy to a therapy recipient. For example, it is possible, using the mixing valve assembly of the instant invention, to provide therapy fluid at incrementally controllable therapy temperatures to a variety of therapy devices including soaking baths, circulation chambers, and the like.

While this invention has been described in terms of several preferred embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A mixing valve assembly operable to deliver an output fluid with a composition determined by a selected ratio of input fluids, said assembly comprising:

an incrementally positionable ball element having an adjustable rotational position within said mixing valve assembly, said ball having continuously varying restrictive inlets, a mixing chamber in fluid communication with said inlets, and an outlet for delivery of said outlet fluid, said outlet being in fluid communication with said mixing chamber wherein said ball is further characterized by spaced apart interior restrictor walls defining on opposite sides thereof inlet chambers and between them said mixing chamber wherein said interior restrictor walls are disposed between said inlet chambers to channel fluids from said inlet chambers to said mixing chamber, and wherein;

said selected ratio is determined by the rotational position of said ball, and wherein each said opening has a corresponding inlet flow resistance, further wherein each said inlet has a size which is proportional to each said corresponding inlet flow resistance, wherein said inlets are substantially wedge shaped, each having a wide forward edge and a narrow rear apex.

2. The mixing valve assembly of claim 1, wherein said assembly is operable to deliver a therapy fluid with an outlet temperature, further wherein said input fluids comprise at least one relatively high temperature and one relatively low temperature fluid, wherein said ball further comprises:

a first inlet for said high temperature fluid, a second inlet for said low temperature fluid, wherein;

said outlet temperature is determined by said selected ratio.

3. The mixing valve assembly of claim 2, wherein said outlet temperature is controlled by adjusting the rotational position of said ball to give any desired outlet temperature profile.

4. The mixing valve assembly of claim 3, wherein incremental rotation of said ball gives a substantially linear outlet temperature profile.

5. The mixing valve assembly of claim 4, wherein said assembly is operable to deliver said therapy fluid at a substantially constant outlet pressure and substantially constant outlet flow rate.

6. The mixing valve assembly of claim 5, wherein said second inlet is larger than said first inlet.

7. The mixing valve assembly of claim 6, wherein said internal restrictor walls include a first wall defining a high temperature inlet chamber and a second wall defining a low temperature inlet chamber.

8. The mixing valve assembly of claim 7 wherein each said wedge shaped inlet extends 140° around the circumference of said ball.

9. The mixing valve assembly of claim 8 wherein the wide forward edge of said first wedge shaped inlet forms a 5° opening at the surface of said ball element, and the wide forward edge of said second wedge shaped inlet forms a 15° opening at the surface of said ball element.

10. The mixing valve assembly of claim 9 wherein said assembly is configured to deliver said therapy fluid to a therapy pad.

11. The mixing valve assembly of claim 10 wherein said therapy pad includes an active thermal exchange bladder and an elastic wrap connected to the thermal exchange bladder, further wherein the elastic wrap is configured to adjustably wrap around the thermal exchange bladder and compress the thermal exchange bladder around a therapy site.

12. The mixing valve assembly of claim 11 further comprising a thermostat that automatically selects the ratio of high temperature and low temperature fluids delivered from the mixing valve assembly.

13. The mixing valve assembly of claim 12 wherein the thermostat is programmable to automatically change the therapy temperature at a desired time by adjusting the ratio of high temperature and low temperature fluids delivered form the mixing valve assembly.

14. The mixing valve assembly of claim 13 wherein the thermostat is programmed to prevent said outlet temperature from going below a pre-set minimum.

15. The mixing valve assembly of claim 14 wherein the thermostat is programmed to prevent said outlet temperature from going below 55 degrees Fahrenheit.

* * * * *